US 6,658,322 B1

(12) United States Patent
Frederick et al.

(10) Patent No.: US 6,658,322 B1
(45) Date of Patent: Dec. 2, 2003

(54) SYSTEM AND METHOD FOR TRACKING MEDICAL ITEMS AND SUPPLIES

(75) Inventors: David T. Frederick, North Hunington, PA (US); James A. Michael, Cranberry Township, PA (US); R. Michael McGrady, Baden, PA (US)

(73) Assignee: MedSelect Inc., Alpharetta, GA (US)

( * ) Notice: Subject to any disclaimer, the term of this patent is extended or adjusted under 35 U.S.C. 154(b) by 48 days.

(21) Appl. No.: 09/848,633

(22) Filed: May 3, 2001

Related U.S. Application Data

(60) Provisional application No. 60/202,508, filed on May 5, 2000.

(51) Int. Cl.⁷ ................................................ G06F 17/00
(52) U.S. Cl. ....................... 700/236; 700/232; 700/242; 700/244
(58) Field of Search ................................. 700/231, 232, 700/236, 237, 241, 242, 244; 221/2

(56) References Cited

U.S. PATENT DOCUMENTS

| | | | |
|---|---|---|---|
| 4,518,208 A | * | 5/1985 | Marder ........................ 211/74 |
| 5,346,297 A | | 9/1994 | Colson, Jr. et al. |
| 5,745,366 A | | 4/1998 | Higham et al. |
| 5,805,455 A | | 9/1998 | Lipps |
| 5,805,456 A | | 9/1998 | Higham et al. |
| 5,905,653 A | | 5/1999 | Higham et al. |
| 5,927,540 A | | 7/1999 | Godiewski |
| 5,940,306 A | | 8/1999 | Gardner et al. |
| 6,011,999 A | | 1/2000 | Holmes |
| 6,039,467 A | | 3/2000 | Holmes |
| 6,109,774 A | * | 8/2000 | Holmes et al. ................ 221/12 |
| 6,116,461 A | | 9/2000 | Broadfield et al. |
| 6,151,536 A | * | 11/2000 | Arnold et al. ............... 700/236 |
| 6,272,394 B1 | * | 8/2001 | Lipps ............................. 221/2 |
| 6,339,732 B1 | * | 1/2002 | Phoon et al. ................ 700/237 |
| 6,385,505 B1 | * | 5/2002 | Lipps ............................. 221/2 |
| 6,401,991 B1 | * | 6/2002 | Eannone ..................... 221/103 |

* cited by examiner

Primary Examiner—Khoi H. Tran
(74) Attorney, Agent, or Firm—Ralph E. Jocke; Daniel D. Wasil; Walker & Jocke

(57) ABSTRACT

The system for controlling and tracking medical items (830) includes one or more computers and associated data stores including information concerning authorized users, patients, medical items that have been prescribed for patients, medical items available, storage locations for medical items and events associated with receiving, dispensing, taking and returning medical items for patients. Authorized users taking medical items from storage locations are enabled to provide inputs through a display terminal (880) to indicate the taking of medical items for patients. Medical items are enabled to be taken from a plurality of storage cabinets (878). Storage cabinets are operative so that users may be guided to find a selected medical item for which corresponding information is input at an associated display terminal. Alternatively, users are enabled to gain access to the interior of the cabinet and indicate through appropriate inputs, the types and quantities of items that are being taken.

30 Claims, 30 Drawing Sheets

| Restock | | | | |
|---|---|---|---|---|
| Position Description | Material Name | Unit of Issue | Item Code | Qty |

| Prev Page | Nursing Name | | Select | Help |
|---|---|---|---|---|
| NextPage | Supply Position | Below Min | Print | Close |

FIG. 25

Stock Amount — 1138

- Position
- Material Name
- Nursing Name
- Unit of Issue
- Current Quantity
- Max Quantity
- Nearest Expiration Date
- Lot Number Restock Quantity Keypad 1139: 1 2 3 / 4 5 6 / 7 8 9 / 0 Clear Buttons: Maximize Quantity | Restock Quantity — 1142 | Accept — 1143 | Help
Discrepancy | Expire Quantity | Unload Quantity | Close

FIG. 26

PATIENT USAGE BROWSER              1084

| PAT_USAGE | | | | |
|---|---|---|---|---|
| Nursing Name | Size | Qty Form | Status | Date/Time UserName |
| Erthromyclyn | | 1 | Taken | 20 Aug 07:30 Frederick |

| Prev Page | Material Name | | Return | Help |
|---|---|---|---|---|
| Next Page | Sort by Supply | | Waste | Close |

| Stockit | | | |
|---|---|---|---|
| Position Description | Trade Name | Unit of Issue | Qty |

Prev Page | Nursing Name | Keypad | Accept | Help
Next Page | Supply Position | Discrepancy | | Cancel

FIG. 31

SYSTEM AND METHOD FOR TRACKING MEDICAL ITEMS AND SUPPLIES

CROSS REFERENCE TO RELATED APPLICATION

This Application claims benefit pursuant to 35 U.S.C. §119(e) of Provisional Application Serial No. 60/202,508 filed May 5, 2000.

TECHNICAL FIELD

This invention relates to devices, systems and methods for controlling and tracking medical items such as medical and surgical supplies. Particularly this invention relates to apparatus and methods for controlling and tracking medical items in hospitals, clinics or other health care settings.

BACKGROUND ART

The treatment of patients in hospitals, clinics and other health care settings usually involves receipt by the patient of medical items. These items may include prescription items such as drugs and medications. Medical treatment may also involve other nonprescription medical items such as medical and surgical supplies, as well as consumable medical equipment. To serve the needs of patients in a health care setting, sufficient stocks of such medical items must be kept available for use. Because such items may be relatively high in cost and/or relatively large quantities of such items may be consumed, it is important for the health care provider to accurately control and track the use of such items and to accurately allocate the charges associated with the use of such items to patients.

Systems and methods for tracking the use of medical items have been previously developed. Examples of such systems and methods are disclosed in U.S. Pat. Nos. 5,404,384; 5,533,079; 5,790,409; 5,848,593; 5,912,818; 5,993,046; 6,019,249; 6,073,834; 6,112,506; 6,141,942; and 6,163,737, the disclosures of all of which are incorporated by reference as if fully rewritten herein.

While the previously developed systems provide useful devices and methods for tracking the use of medical items, further improvements are possible. Specifically, persons who must obtain medical and surgical supply items from storage may wish to do so more quickly while still maintaining adequate security and tracking of the items. In addition, persons who are taking such medical items from storage may often know exactly where a particular desired item is located and may benefit by being able to access and take the item with a minimum of delay. In other cases, persons may be unfamiliar with the location of a particular desired item. In such situations a person may benefit by having a system which guides the user to a particular item that they have indicated that they wish to find. In other situations, persons may wish to take from adjacent storage locations a number of different types of medical items. In such cases the medical professional taking such items may wish to take the items during a single occasion when a lockable storage cabinet or other controlled storage location has been opened. In such cases it may be useful for the person to indicate to the system the types and quantities of each medical item they are taking as quickly as possible.

Thus there exists a need for improved methods and systems for controlling and tracking the taking of medical items.

DISCLOSURE OF INVENTION

It is an object of an exemplary form of the present invention to provide a system for controlling and tracking medical items.

It is a further object of an exemplary form of the present invention to provide a system for controlling and tracking medical items that can be used to track the use of medical and surgical supplies.

It is a farther object of an exemplary form of the present invention to provide a system for controlling and tracking medical items that enables an authorized user to take items from storage and record such taking quickly.

It is a further object of an exemplary form of the present invention to provide a system for controlling and tracking medical items that enables a user to be guided to a storage location where a particular type medical item desired by the user is stored.

It is a further object of an exemplary form of the present invention to provide a system for controlling and tracking medical items that enables an authorized user to take and indicate the taking of a plurality of different types of medical items.

It is a further object of an exemplary form of the present invention to provide a method for controlling and tracking medical items which enables a user to indicate the taking of additional items or to change the indication of the types of items being taken after the user has gained access to a controlled access storage location.

It is a further object of an exemplary form of the present invention to provide a system for controlling and tracking medical items that includes a user interface that is readily used and operated by users taking medical items from controlled storage areas.

It is a further object of an exemplary form of the present invention to provide a system for controlling and tracking medical items that includes a storage cabinet with configurable shelves, which shelves include storage locations that may be correlated to input devices on a user interface.

It is a further object of an exemplary form of the present invention to provide a system for controlling and tracking medical items that includes a versatile storage cabinet structure.

It is a further object of an exemplary form of the present invention to provide a method for controlling and tracking the taking of medical items from controlled access storage areas within a storage cabinet.

It is a further object of an exemplary form of the present invention to provide a method for controlling and tracking the taking of medical items from a storage cabinet that enables users to indicate the types and quantities of medical items being taken proximate to the time of such taking.

It is a further object of an exemplary form of the present invention to provide a method for controlling and tracking the taking of medical items from a storage cabinet that includes the capabilities of guiding a user to a storage location for a requested type of medical item.

It is a further object of an exemplary form of the present invention to provide a method for controlling and tracking the taking of medical items from a storage cabinet that enables a user to indicate and change the types and quantities of medical items being taken once access to the cabinet has been gained.

It is a further object of an exemplary form of the present invention to provide a method for controlling and tracking the taking of medical items from a cabinet that provides fast and efficient tracking and removal of medical items.

Further objects of-exemplary forms of the present invention will be made apparent in the following Best Modes For Carrying Out Invention and the appended claims.

The foregoing objects are accomplished in an exemplary form of the present invention through use of a method and system which includes a storage cabinet for holding medical items such as medical and surgical supplies. The storage cabinet includes a plurality of lockable doors which control access to the interior thereof.

The cabinet includes a plurality of shelves in supporting connection with the interior of the cabinet. In embodiments of the invention the shelves may be stationary shelves or pullout type shelves. The shelves include storage locations or areas for storing medical items.

Certain shelves in exemplary embodiments of the invention include a shelf interface located adjacent a front portion of a storage shelf. The shelf interface comprises a user interface that includes a plurality of push buttons. The shelf interface further includes a plurality of visual indicators, each such indicator being uniquely associated with one of the plurality of buttons.

The shelf interface of the exemplary embodiment further includes a numerical keypad for manually inputting numerical values. The shelf interface further includes a shelf display for providing a visual output including quantity values. The exemplary embodiment of the shelf interface further includes a clear indicator that may be used for clearing inputs previously made to the system through input devices.

In the exemplary embodiment storage locations are correlated with particular buttons on the shelf interface. This is done in an exemplary embodiment by applying indicia such as corresponding self-adhesive labels to a storage location and to the corresponding button which may be used to indicate to the system the removal or addition of medical items stored in the storage location.

The exemplary embodiment of the present invention further includes a terminal that is accessible eternally relative to the cabinet. The terminal may be a display terminal of the type described in connection with the incorporated patent disclosures. The terminal enables users to provide inputs and receive outputs from one or more processors operating in connection with the system. In the exemplary embodiment the terminal may be used by a user to input user identifying information. The terminal in the exemplary embodiment may also be used for providing inputs from a user including selections related to patients, medical items, quantities or other values pertinent to the tracking of the medical items stored in the cabinet.

In the exemplary embodiment of the invention, an authorized user is enabled to obtain medical items from the cabinet and to record the taking thereof in at least two ways. In accordance with a first approach, a user after being identified as authorized to use the system, indicates their desire to generally access medical items stored in the storage cabinet. In response to an indicative input to the terminal, doors on the cabinet which control access items to which the particular user is authorized to have access, are unlocked. In the exemplary embodiment a visual indication is given to indicate which doors are unlocked. The user may then open these doors and take the medical items from the storage locations. To record the taking of each medical item, the user in the exemplary embodiment touches the button on the shelf interface corresponding to the storage location on the shelf from which a medical item is being taken to identify the particular type of medical item to the system. The user also inputs the quantity of the type medical item being taken from the identified storage location through the numerical keypad on the corresponding shelf interface. When the user inputs such a value, the value is displayed on the shelf display.

If the user should make a mistake in indicating the type or number of medical item being taken, the user may clear the incorrect input by pressing the clear indicator. The user may then enter correct type and quantity data. The user may repeat this process for a plurality of medical items located in different storage locations. Once the user has provided inputs to indicate the taking of medical items from the cabinet, the taking of such items is recorded in a data store.

Alternatively in the exemplary embodiment, a user may input information corresponding to a particular type medical item (or a plurality of types) that the user wishes to find within the cabinet. In response to an authorized user providing such inputs, the cabinet door (or doors) controlling access to the shelf or shelves, in which the selected medical items are stored, will unlock. The unlocking of the doors in the exemplary embodiment is indicated through activation of visual indicators associated with the doors. While taking such medical items, the visual indicators corresponding to the storage location identifying buttons will be activated to indicate to the user where the selected medical item or items are located. In the exemplary embodiment color-coding is used as the visual indicia, which correlates the buttons and the storage locations. This enables the user to quickly find the requested medical items even though each storage location is generally not in proximity to its corresponding visual indicator.

In the exemplary embodiment when the user is requesting of the system to "find" medical items, the quantity of each particular item requested is displayed through the shelf display. In cases where multiple items from the same shelf have been selected, the user can verify the quantity of each item that they have previously selected through the display terminal by touching the particular button corresponding to the item. This causes the selected quantity to be output through the display. Further in the exemplary embodiment, in the event that the user determines once they have accessed a storage location that they wish to take different quantities or other types of medical items, they may do so through use of the clear indicator and the buttons and numerical keypad on the shelf interface. Such approaches enable a user to modify or add to the types and quantities of medical items being notified to the system as taken during the course of a single occasion when the particular storage shelf is accessed. Once the user has provided the corresponding inputs and taken all of the desired medical items, the taking of such items is recorded in a database.

BRIEF DESCRIPTION OF DRAWINGS

FIGS. 23–31 are views of exemplary screen outputs presented on a display terminal in connection with the operation of the exemplary supply cabinet as represented in FIGS. 19–22.

BEST MODES FOR CARRYING OUT INVENTION

Figure 1:
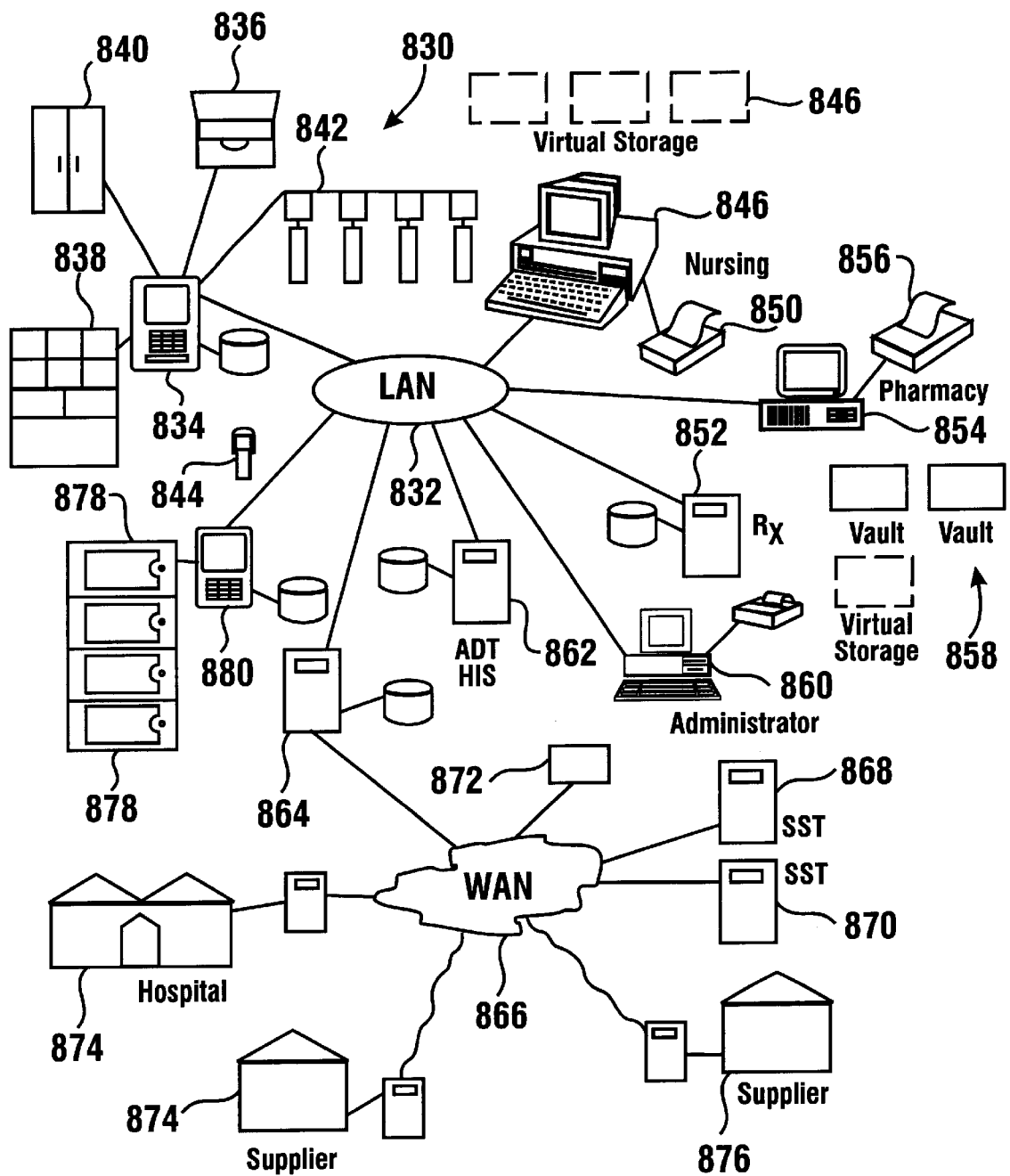
FIG. 1 is a schematic view of an exemplary form of a system of the present invention that includes features for tracking and controlling the taking of medical items from a supply cabinet.

Referring now to the drawings and particularly to FIG. 1 there is shown a system generally indicated 830 including an exemplary embodiment of the present invention. System 830 is generally similar to system 322 shown in FIG. 40 of U.S. Pat. Nos. 6,112,501 and 5,912,818, the disclosures of which patents are incorporated herein. Components and features discussed in each of these previously described systems may be used in connection with system 830. It should be understood that in some embodiments these components may be included and may operate in system 830 in a manner similar to that described in the incorporated disclosures. Various combinations of components and features described in such incorporated disclosures may be used in connection with system 830 even though not schematically represented in FIG. 1.

System 830 includes a local area network 832 that provides for electronic communication between components of the system. It should be understood that local area network 832 may be one or more interconnected systems which enable devices to communicate. Local area network 832 may extend within a single facility such as a single hospital or a clinic. Alternatively, local area network 832 may be a private network that extends between a group of facilities in which various components of the system are positioned.

In connection with local area network 832 are a plurality of display terminals schematically represented by a display terminal 834. Display terminal 834 in exemplary embodiments may be similar to display terminals 76, 98, 102, 338 described in the incorporated patent disclosures. Display terminal 834 has in connection therewith one or more computer memories or data stores schematically shown, which hold information and/or programs. Display terminal 834 is operatively connected to devices for controlling access to medical items. These devices are schematically represented as a medication dispenser 836, an electronic lock drawer 838, an electronic lock cabinet 840 and hook registers 842. Of course, various types of other devices, which include storage locations for medical items, may be used in connection in embodiments of the system. Reading devices such as reading device 844 which may be similar to reading device 348 of the incorporated patent disclosure and/or other reading devices may also be used in connection with the system.

Local area network 832 is also in connection with other computers such as nursing station computer 846. Nursing station computer 846 is representative of the computers that may be placed at nursing stations in a hospital or similar facility. Such computers may be used to provide inputs to the system concerning activities involving the treatment of patients. Nursing computer 846 may be used to also receive information such as information relating to medications and treatments which have been prescribed for various patients within the institution. Nursing station computer 846 may in some embodiments be used as an alternative to display terminal 834, and may also be used for tracking medical items in situations where automated types of storage and dispensing devices are not available. Nursing station computer 846 may be used to provide information concerning items taken or replaced in storage areas adjacent to the nursing station. The system may record the status of storage locations which users can access adjacent to the nursing station computer. The system may keep track of medical items stored in such storage locations in a manner similar to that used to track medical items which are removed from or added to other storage locations in the system. The tracking of medical items in such storage locations are represented in FIG. 1 as virtual storage areas 848. Nursing station computer 846 may also have in connection therewith an output device such as a printer 850 for purposes of printing reports related to activities occurring or scheduled to occur.

Local area network 832 in the exemplary embodiment is also in connection with one or more additional computers. Such computers may include, for example, computer 852. Computer 852 in the exemplary embodiment is operative to store and process information concerning medical items in storage locations, patients and medications prescribed for such patients, authorized users of the system, the taking and giving of medications for patients, as well as other information of the types discussed in the incorporated patent disclosures. In addition in the exemplary embodiment computer 852 is operative to store information concerning activities in the pharmacy. One or more pharmacy terminals 854 is in connection with the local area network 832 for purposes of communicating information with appropriately connected computers. Pharmacy terminal 854 includes output devices such as a printer 856. Printer 856 may be used for printing reports. Storage enclosures or facilities such as vaults 858 are also schematically indicated in the pharmacy. The storage vaults may include access controlled storage areas. Such storage vaults may be manually controlled by the system or electronically controlled to limit access to authorized persons.

Exemplary system 830 further includes administrative terminals schematically represented by an administrative terminal 860. Administrative terminal 860 in the exemplary embodiment may be used for programming the system, setting up storage locations, enabling users to selectively operate aspects of the system, monitoring activities and for engaging in other types of activities such as those discussed in the incorporated patent disclosures.

Network 832 is also in operative connection with one or more other computers schematically represented 862. Computer 862 may be used in the exemplary embodiment to process other information such as information in the facility's hospital information system (HIS) or in a facility's admission discharge and transfer (ADT) system. Of course in other embodiments many other types of systems may be in connection with network 832.

System 830 further includes one or more computers schematically indicated 864 which serve as a gateway to other systems. In the exemplary embodiment, computer 864 serves as a firewall for limiting access to and from network 832. As schematically indicated in FIG. 1, computer 864 enables access to a wide area network 866 such as the Internet.

Wide area network 866 is schematically shown connected to a variety of other types of exemplary computers and systems. For example, network 866 may be operatively connected to self service medication dispensers 868, 870. Wide area network 866 may also be in connection with other computers such as a financial transaction processing computer 872. Financial transaction processing computers may be operative to settle accounts, between various entities connected to the system such as a hospital and its employees and/or suppliers. Alternatively, financial transaction computers may be used for the hospital to receive or make payments from third parties such as insurers or other hospitals such as hospital 874 schematically indicated in FIG. 1. Suppliers who are in communication with network 866 are schematically represented 874 and 876. It should be understood that many additional types of providers of goods or services may be connected through one or more networks to the system 832.

In exemplary system 830 shown in FIG. 1, medical items may be obtained from a supply cabinet schematically indicated 878. Cabinet 878 is in operative connection with a display terminal 880. Cabinet 878 is used to control access to a plurality of different types of medical items held therein. Items stored in the cabinet are enabled to be accessed by authorized users of the system in response to inputs to the system and/or the display terminal in a manner similar to that previously discussed. It should be understood that a plurality of cabinets 878 may be used in connection with a single display terminal or other adjacent computer.

Figure 2:
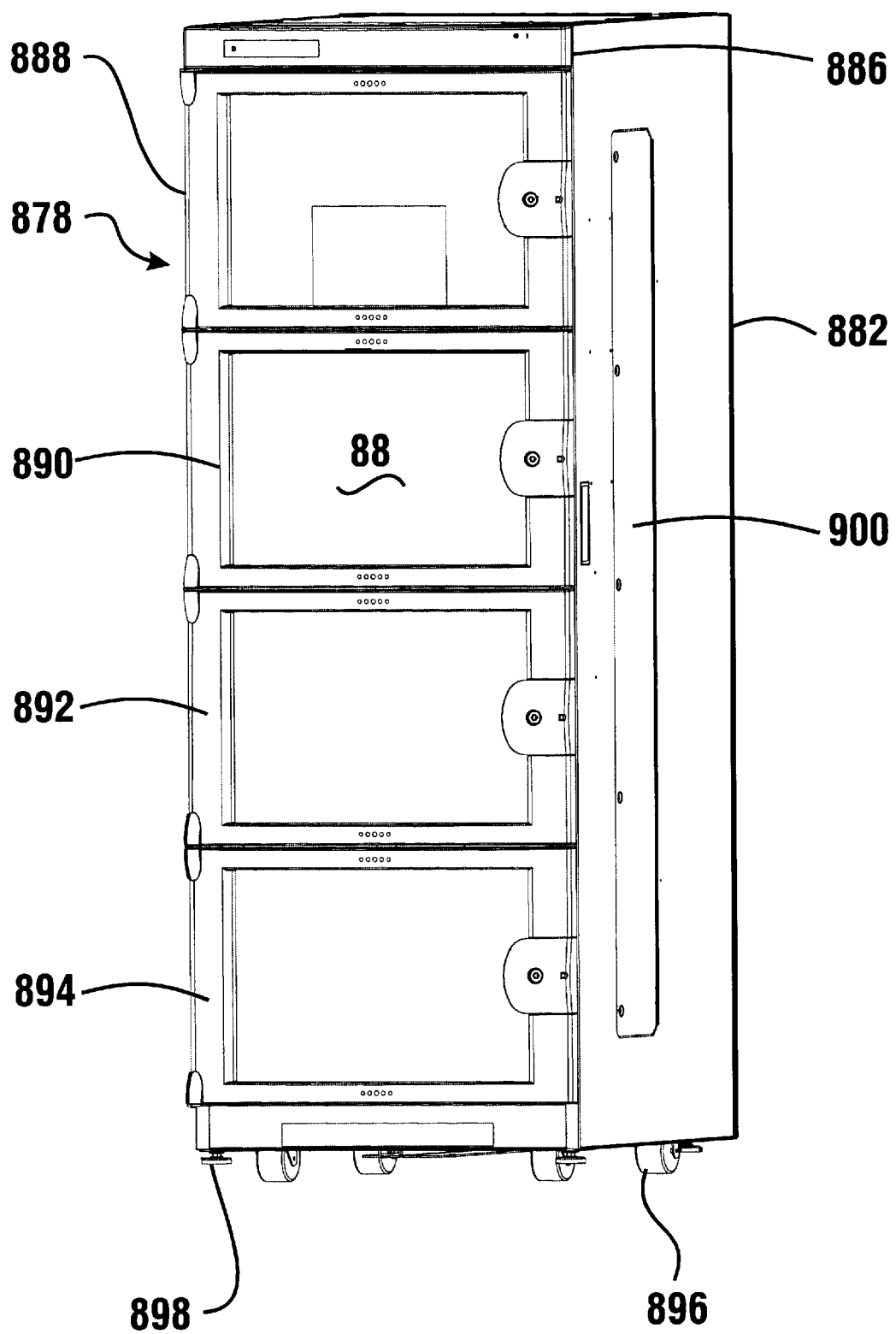
FIG. 2 is an isometric view of an exemplary embodiment of a supply cabinet.

The structure of an exemplary form of the medical item holding cabinet 868 is now described in detail with reference to FIGS. 2–17. As shown in FIG. 2, cabinet 878 includes a generally rectangular housing 882. Housing 882 includes a pair of side walls, top and bottom walls and a back wall which defines an interior area 884. Interior area 884 is accessible through a front opening 886 (see FIG. 3). Opening 886 is divided into regions or areas, each of which may be selectively accessed through corresponding lockable doors 888, 890, 892 and 894. The exemplary embodiment of cabinet 878 includes casters 896 to facilitate occasional but infrequent movement of a cabinet. Cabinet 878 further includes levelers 898. Levelers 898 can be selectively adjusted to engage a surface such as a floor on which the cabinet is supported and to hold the cabinet in a stationary position supported on the levelers instead of or in addition to the casters. Exemplary cabinet 878 further includes a light access door 900. Light access door 900, as later explained, may be used for accessing lighting elements which illuminate the interior area 884 of the cabinet.

Figure 3:
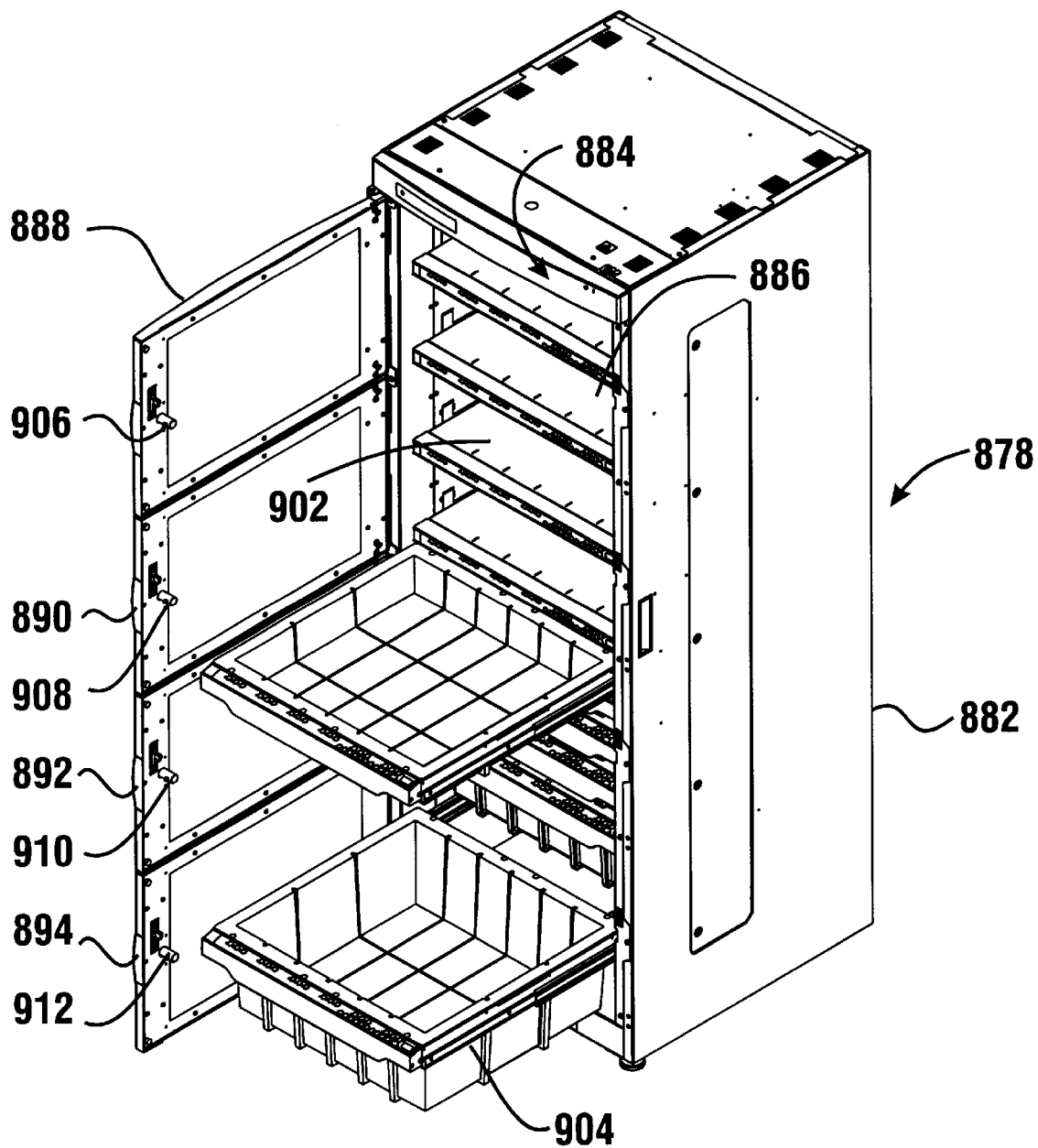
FIG. 3 is an isometric view of the supply cabinet shown in FIG. 2 with the doors open and the pullout shelves extended.

As shown in FIG. 3 in the exemplary embodiment of the cabinet 878, a plurality of shelves are housed in the interior area 884. The shelves may include stationary shelves such as shelf 902 as well as pullout shelves as represented by shelf 904. Each of the stationary shelves and pullout shelves is positioned in the interior area 884 behind a selected one of the doors 888, 890, 892 or 894. In this way, opening selected ones of the doors enables accessing certain shelves in the interior area, and the medical items stored in storage locations on such shelves.

Each of the doors 888, 890, 892 and 894 in the exemplary embodiment includes both a mechanical lock and an electronic lock. Each door includes a bolt 906, 908, 910 and 912. Each of the bolts operatively engages a strike mechanism later described in detail. The cooperating bolt and strike mechanisms enable selectively holding each door in either a locked or unlocked condition. The display terminal 880 in operative connection with the cabinet 878 enables selectively locking and unlocking the doors electronically so as to control access to medical items which are accessible on shelves positioned behind each respective door.

Figure 4:
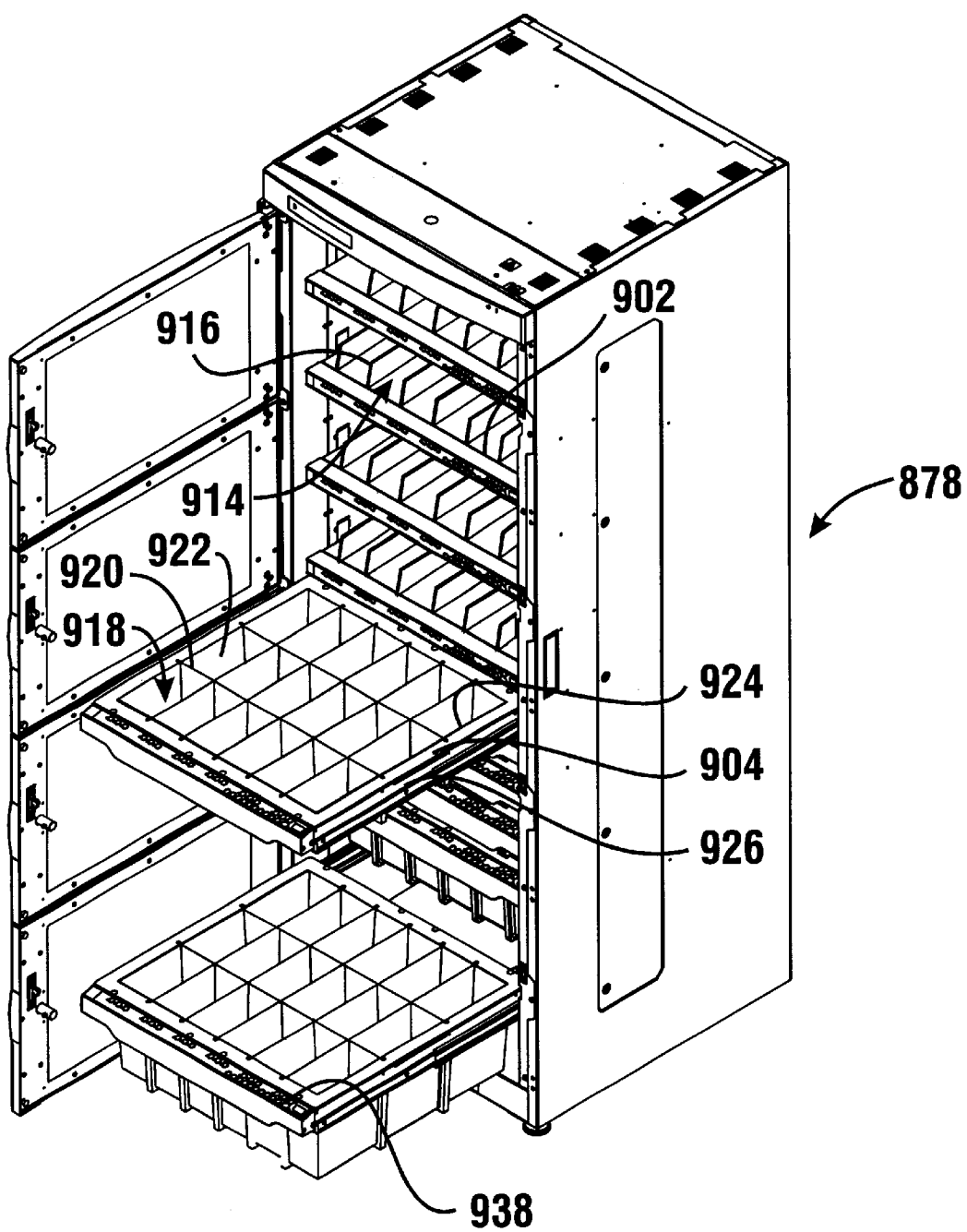
FIG. 4 is a view similar to FIG. 3 showing the shelves and dividers installed in the supply cabinet.

As shown in greater detail in FIG. 4, cabinet 878 has a plurality of storage locations therein. In the exemplary form of the invention, stationary shelves such as shelf 902 include a plurality of transversely spaced storage locations 914. Storage locations 914 are suitable for holding one or more medical items which can be suitably positioned within the elongated storage location. As can be appreciated, a plurality of medical items maybe stacked in abutting relation within each storage location. The storage locations 914 are delineated by dividers 916. Dividers 916 may be transversely positioned in varied locations on the shelf so as to accommodate different sized medical items.

In some alternative embodiments additional dividers (not separately shown) may extend perpendicularly between dividers 916. Such perpendicularly extending dividers may be used to form multiple segregated storage locations between an adjacent pair of dividers 916. Further in other alternative embodiments movable holding devices such as a movable liner may be positioned between an adjacent pair of dividers. Such a liner may include one or more internal walls which bound one or more storage positions within the liner. Examples of such storage liners that may be movably positioned between adjacent dividers on shelf 902 are shown and described in U.S. Pat. No. 6,112,502 which is incorporated by reference as if fully rewritten herein. Such movable liners may be positioned in supporting connection with a shelf such as shelf 902, and pulled outward or removed by a user for purposes of observing the storage areas and medical items held therein.

Pullout shelves such as pullout shelf 904 may also include storage locations schematically indicated 918. Storage locations 918 are defined by dividers 920. Dividers 920 extend in a housing 922. Housing 922 is supported in a frame 924. The frame 924 is extendable from the interior area on slides 926.

Figure 6:
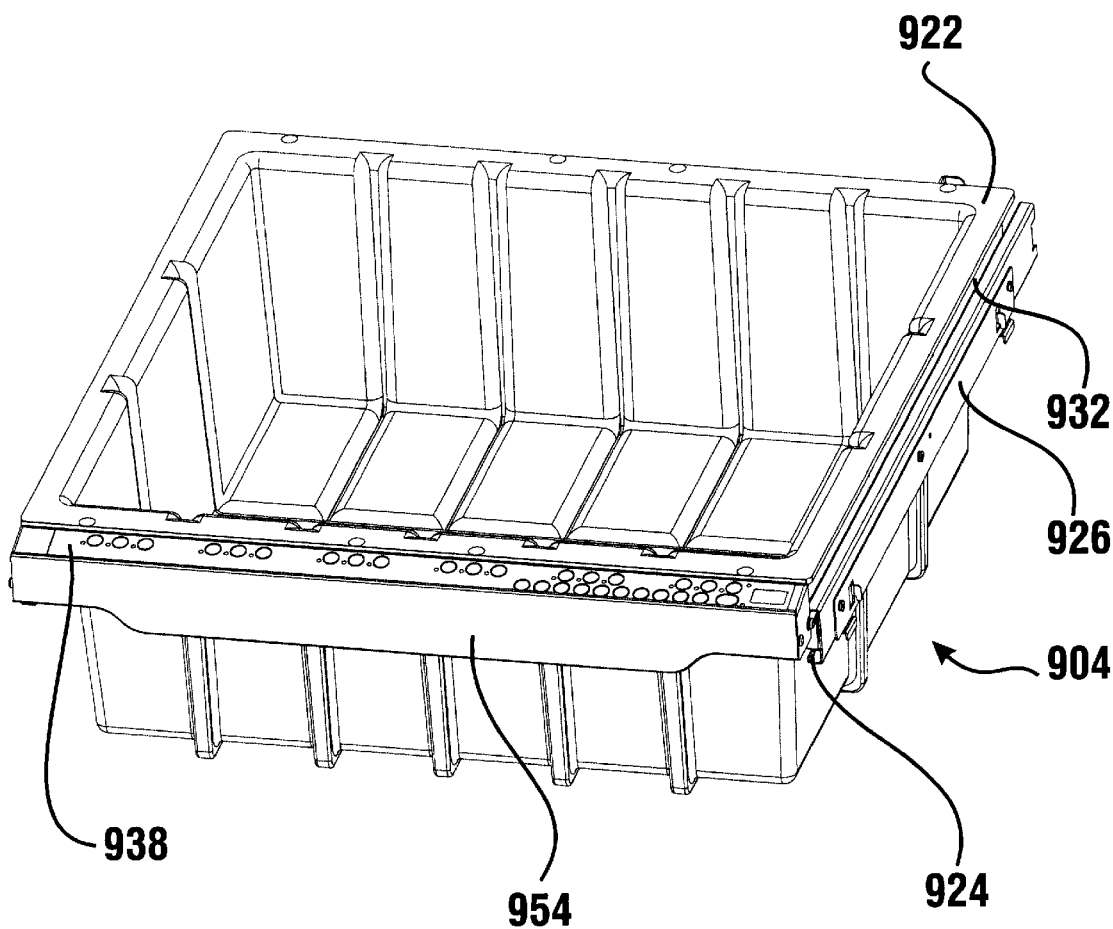
FIG. 6 is an isometric view of an exemplary pullout shelf.
Figure 7:
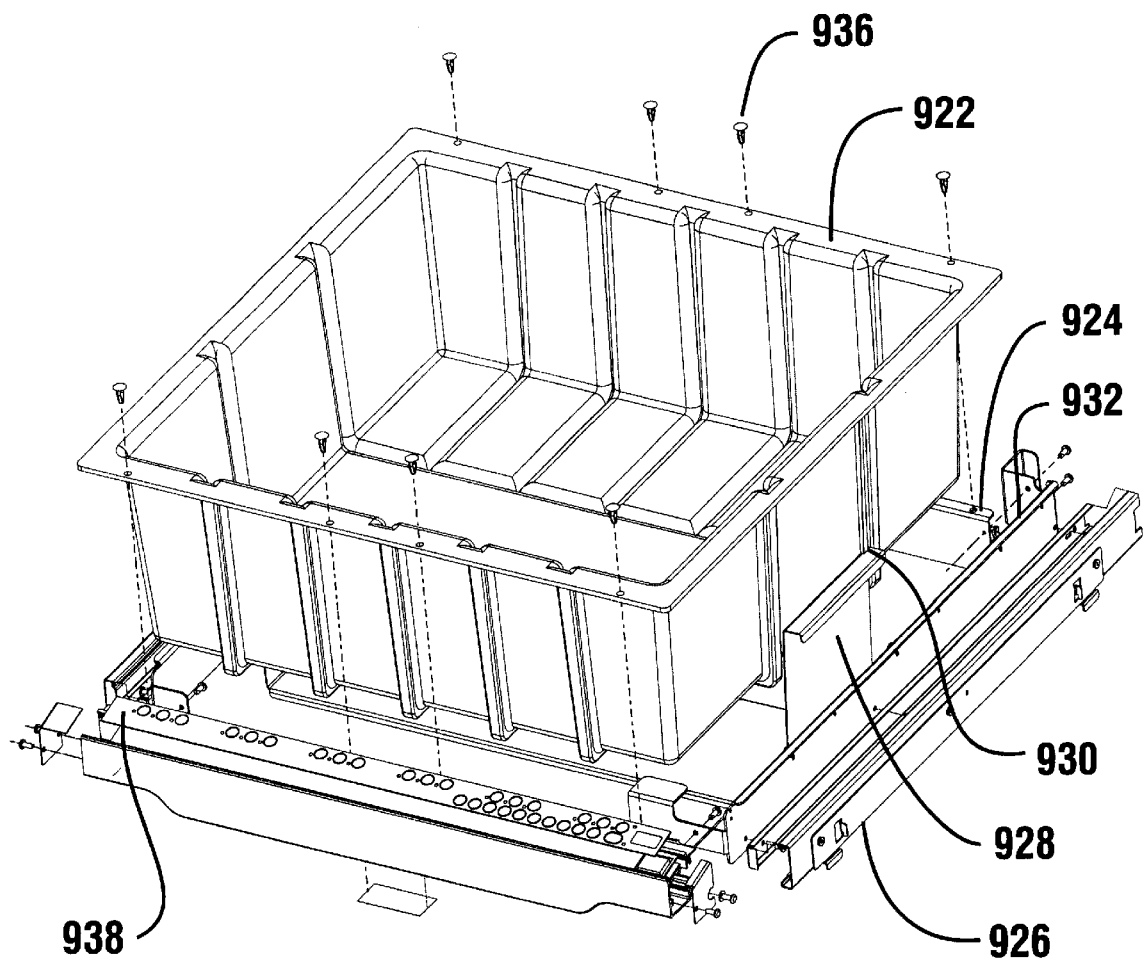
FIG. 7 is an exploded view of the pullout shelf shown in FIG. 6.
Figure 8:
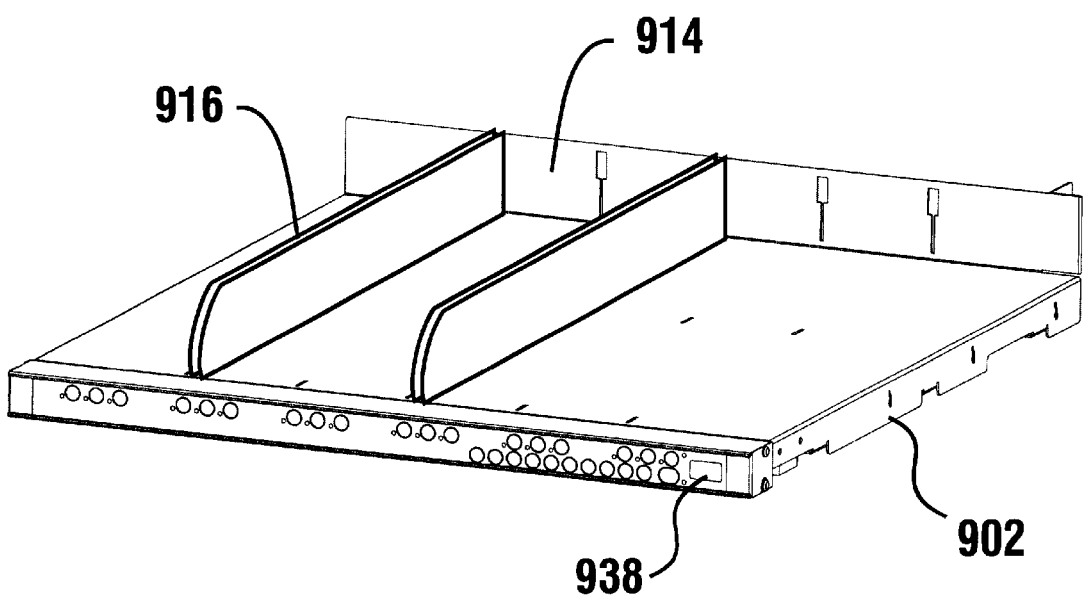
FIG. 8 is an isometric view of a stationary shelf

As best shown in FIGS. 6 and 7, housing 922 in the exemplary embodiment includes a drop in liner which is supported on the frame 924. The frame includes a support bracket 928 which extends transversely under the housing 922 to provide additional support. The support bracket 928 includes angled engaging portions 930 which extend outward and engage the side members 932 of the frame. It should be understood that for some housings 922 which are not intended to support substantial weight, the support bracket 928 may not need to be used. In such situations, the support bracket need not be installed and the housing is supported by its edges on the frame. As can be appreciated, the construction of the exemplary embodiment facilitates the use of either-housings which are intended to hold considerable mass such as the deep housing shown in FIG. 7 or, alternatively, relatively shallow housings for holding lower mass supported in the same type of basic pullout drawer structure. Shelves may have various arrangements of dividers therein. Further as represented by fasteners 936 in FIG. 7, housings 922 may be releasably fastened to the supporting frame 924. Alternatively housings may be supported in the frame without being fastened thereto.

In the exemplary embodiment of the cabinet 878, each of the stationary shelves and rollout shelves include a shelf interface 938. Shelf interface 938 is shown in greater detail in FIG. 5. Shelf interface 938 in the exemplary embodiment includes a user interface with a plurality of finger actuatable push buttons 940. Each push button 940 has an indicator 942 associated therewith. In the embodiment shown, the indicators include an LED which illuminates in appropriate circumstances later described, to identify a particular button which button can be correlated with a storage location. In the exemplary embodiment, each shelf interface includes 18 buttons 940 each having an associated indicator 942. Of course, in other embodiments, other numbers and/or types of actuators other than buttons, or indicators other than illumination type indicators may be used.

Exemplary shelf interface 938 further includes a keypad 944. Keypad 944 includes numerals zero (0) through nine (9) which can be manually actuated by a user for purposes which are later discussed. The shelf interface 938 also includes a "clear" button 946. The clear button is used to clear or delete from the system an incorrect input. A display 948 is also included on the exemplary shelf interface. In the embodiment shown, display 948 is a two (2) character display such that it may output a two-digit value. Shelf interface 938 also includes a "take" indicator 950 and a "return" indicator 952 positioned adjacent to the display. In the exemplary embodiment, the take and return indicators comprise illuminated indicators such as LEDs. Of course in other embodiments other numbers and types of indicators may be used. It should be understood that in other embodiments the display 948 or indicators 950, 952 or both may be located elsewhere on the cabinet rather than the shelf.

As shown in FIG. 4, each of the stationary and pullout shelves includes a shelf interface. As shown in the exemplary stationary shelf 902 in FIG. 8, the shelf interface 938 extends generally vertically on a front portion of the shelf frame. This enables a user viewing a stationary shelf to observe the shelf interface as well as medical items located in storage locations 914 which extend between the dividers. As shown in FIG. 4, in the exemplary form of the invention, stationary shelves 902 are generally positioned in the upper area of the cabinet 878 so that the stationary shelves are closer to eye level which facilitates a user's ability to observe the shelf interface 938 and the storage locations.

As best shown in FIG. 6 on the pullout shelves such as shelf 904, the shelf interface 938 is positioned adjacent the front portion of the shelf frame 924 and extends at an angle such that the interface is facing both forward and upward relative to the shelf. The shelf interface 938 in the exemplary embodiment is supported on a handle portion 954 adjacent the front of the frame. As shown in FIG. 4, pullout shelves may be positioned in areas of the cabinet 878 so that a user can see the shelf interface generally without having to stoop or bend down. This enables the user to see the indicators and actuate buttons on the shelf interface of the pullout shelves so as to provide inputs to the system. Further the position of the shelf interface on the pullout shelf enables a user to view the indicators and have access to the input devices even though the shelf is fully retracted into the interior area of the cabinet.

In the exemplary embodiment of the present invention, the shelf interface 938 comprises a flexible circuit which has the buttons and indicators integrated therein. The flexible circuit is enabled to be positioned in an elongated slot that is integral with the front portions of both the stationary shelves or pullout shelves. This facilitates the construction of the shelves as well as replacement of any shelf interface units which may sustain a malfunction. Alternative embodiments may have alternative positions for supporting the shelf interface or may provide a movably positionable surface for the shelf interface so that the interface position may be selectively tailored to the position of the shelf in the cabinet. This may be done for example by supporting the shelf interface on a surface that is selectively angularly movable.

While the exemplary embodiment of the cabinet 878 has been shown with both stationary shelves and pullout shelves, it should be understood that embodiments of the invention may include only one shelf type. Further, while the exemplary form of the cabinet 878 has been shown with shelves, each of which has a shelf interface, it should be understood that in some embodiments, shelves may be included which do not have a shelf interface. Embodiments of the invention may have shelves of either type in which a shelf has no shelf interface. This may include for example where multiple shelves contain the same type of medical item and a single shelf interface is used to provide inputs related to medical items stored on multiple shelves. It should be further understood that alternative embodiments of the invention may include within the interior of the cabinet, fixed dividing walls. Such fixed dividing walls may be used to reduce the risk that a person who is authorized to receive access to one area of the cabinet may improperly access medical items located in another part of the cabinet to which that user is not authorized to have access such as by using a tool, probe or other device.

Figure 9:
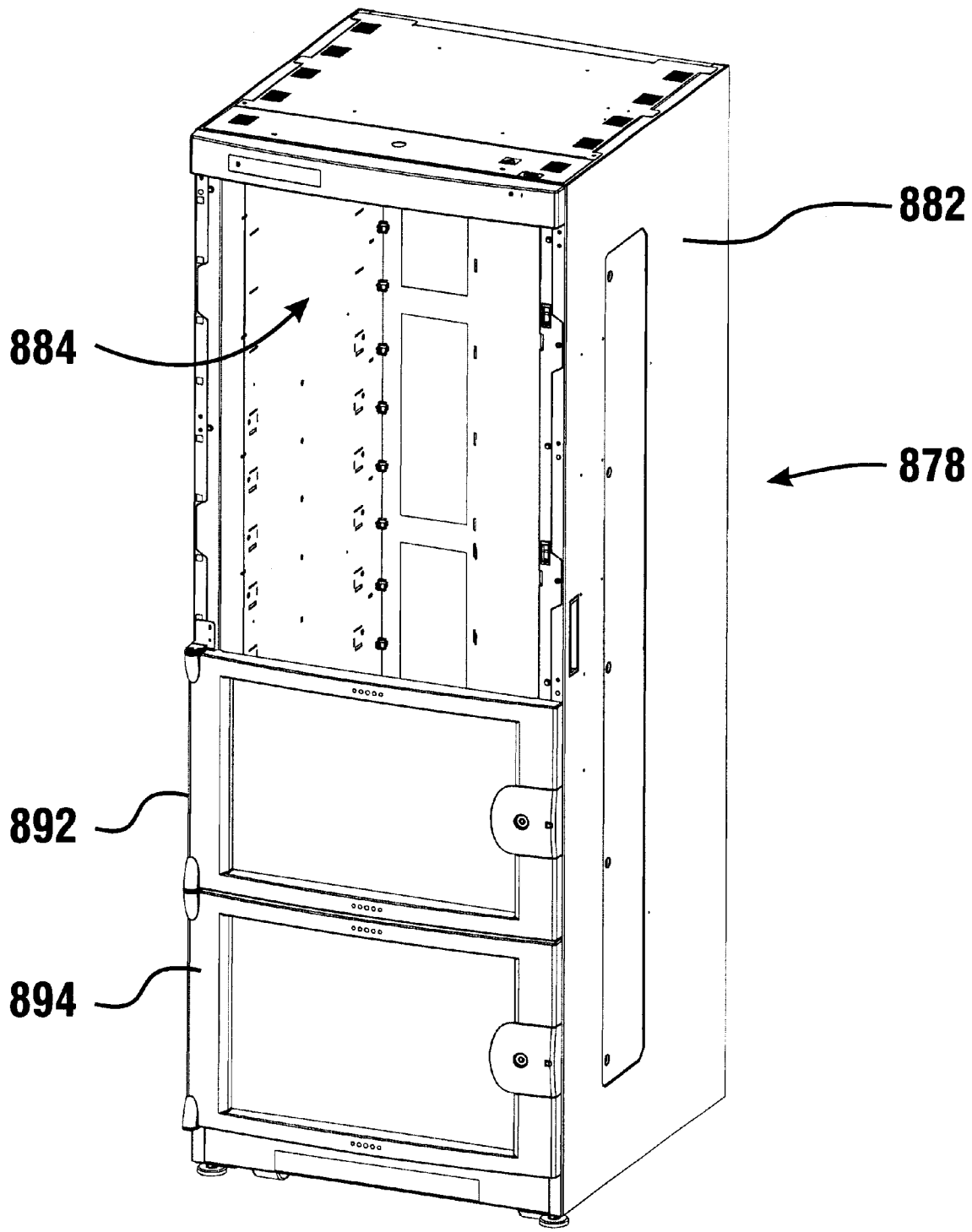
FIG. 9 is an isometric view of the cabinet shown in FIG. 2 showing the interior features used for mounting stationary and pullout shelves.

FIG. 9 shows the cabinet 878 in a state of partial assembly in which only two of the doors have been installed thereon. As can be seen in FIG. 9, the interior area 884 of the housing 882 is bounded by walls which include mounting means therein. These mounting means in the exemplary embodiment include perforations in inner walls which are suitable for supporting brackets. Such brackets may be stationary brackets such as are used with stationary shelves or slide brackets such as may be used to support pullout shelves. Also in the exemplary form of the invention, housing 882 is constructed such that the doors may be mounted in a left hand or right hand configuration on the cabinet. This facilitates flexibility in the construction and enables convenient mounting of the cabinet so as to be readily accessible even when the cabinet is positioned adjacent to walls, doors and the like. As can be appreciated, in the exemplary embodiment the cabinet doors are made generally symmetrical such that the doors may be mounted to the cabinet in a left hand or right hand configuration by inverse mounting. The vertically extending side walls of the housing are made such that openings are provided in each for mounting the door hinge supports and mounting associated parts of the locking mechanisms on either side of the cabinet. This further facilitates flexibility of the system. It should be understood, however, that embodiments of the invention need not necessarily include these features.

Figure 10:
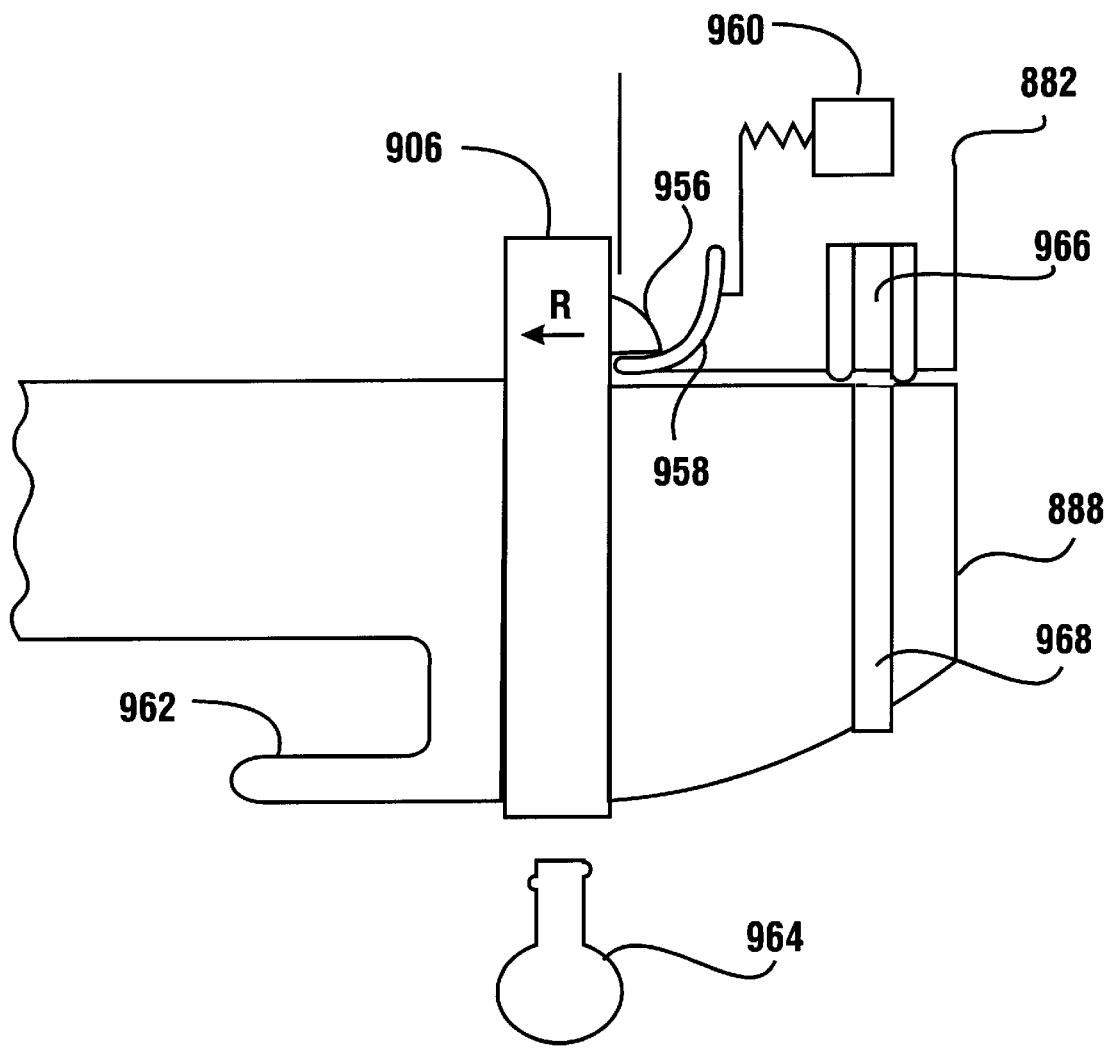
FIG. 10 is a top cross-sectional view of the light indicator on a door of the supply cabinet shown in FIG. 2.

FIG. 10 shows a top schematic view of an exemplary door 888 in closed position adjacent to housing 882. The right hand side of the door as shown is positioned adjacent to the vertically extending side wall of the housing 882. The bolt 906 which is operatively attached to the door includes a retractable portion 956. Retractable portion 956 normally extends outward from the bolt. As shown in the closed position of the door, the retractable portion 956 engages a striker plate 958 in supporting connection with the cabinet wall. Striker plate 958 is in operative connection with an actuator 960. In the position of the striker plate shown in FIG. 10, the striker plate 958 prevents the retractable portion 956 from moving forward as shown and thus maintains the door 888 closed when in a locked position. In response to signals from the display terminal or other device, the actuator 960 is enabled to move the striker plate 958 such that the portion 950 is no longer prevented from moving forward thereby. This enables the door 888 to be opened. Outward movement of the door is facilitated by a handle portion 962 on the exterior of the door frame.

In the exemplary embodiment, the bolt 906 may alternatively be actuated through a mechanical locking mechanism using a key schematically shown as 964. By insertion of the key into an external lock mechanical actuator connected to the bolt, the retractable portion 956 is enabled to be retracted in the direction of arrow "R" in FIG. 10. This enables the door 888 to be opened even though the actuator 960 is not electronically opened by the display terminal. In this way, the interior area of the cabinet may be accessed by authorized persons in cases where there has been a power failure or other malfunction of the system. In an exemplary embodiment holding devices such as spring biased latches, magnetic latches or similar devices are operatively connected to each door. These holding devices operate to keep an unlocked door in a closed position until it is pulled open by a user. This avoids unwanted opening of unlocked doors which may interfere in taking medical items that are accessed behind other doors.

Another useful aspect of the exemplary embodiment of the invention are indicators that are provided on each of the doors without the need for wiring for other electrical connections thereto. This is achieved through use of illuminating devices such as LEDs positioned in the side walls of the housing 882. Such LEDs are represented by LED 966 in FIG. 10. In the closed position of the adjacent door 888, LED 966 is in alignment with a light guide 968 which extends through the door to the face thereof.

In the-exemplary embodiment, when the display terminal or other device is operative to actuate actuator 960 so as to place the door in an open condition, signals from the display terminal or device are operative to illuminate the associated LED 966. The illumination of the LED is visible through the light guide 968 on the face of the door housing. In this way, a user is given an indication of doors that have been placed in an unlocked condition and which storage locations can be accessed. This construction enables such indications to be given without having lights or other indicators electrically connected in the door.

In some embodiments multiple doors may be connected together. This enables a user to access a larger portion of the interior of the cabinet through a single door opening motion. In such cases all of the electronic locks which enable opening of the plurality of connected doors may be activated simultaneously so that the connected doors are unlocked and locked together. In some embodiments the indicators associated with all of the connected doors may be activated to indicate the condition of each one of the doors. Alternatively, systems may be configured so that only a single indicator is activated to indicate the condition of multiple connected doors. In some embodiments the single indicator may be one positioned adjacent to a door handle of the door that is preferably manually engaged when opening the multiple connected doors. Of course in other embodiments other approaches may be used.

The exemplary embodiment of the cabinet 878 provides enhanced resistance to unwanted movement such as tipping. As can be appreciated, if a substantial number of pullout shelves are included in the cabinet, and if a substantial amount of mass is moved outward by extending pullout shelves, the cabinet may have a tendency to tip forward.

Figure 11:
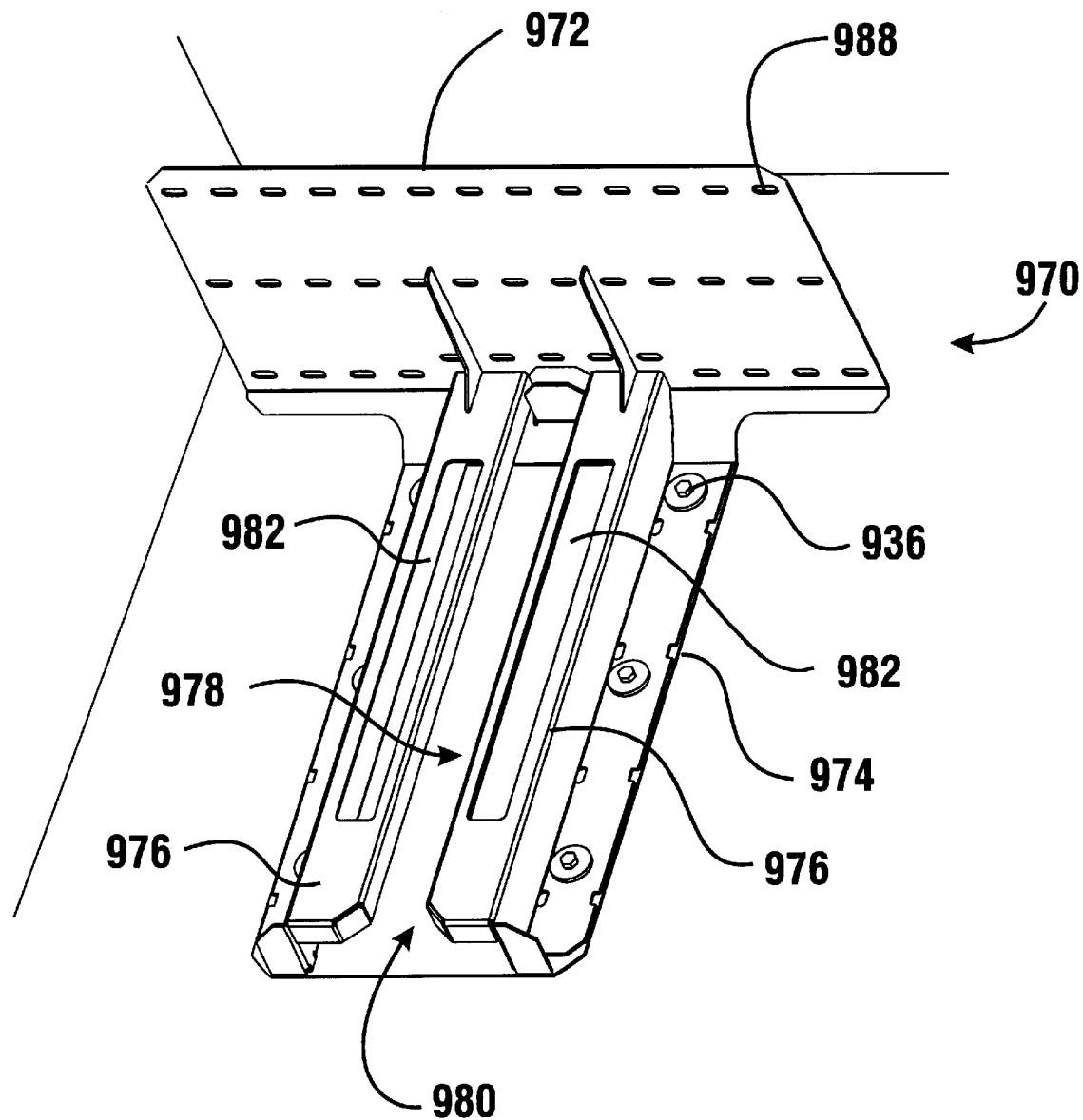
FIG. 11 is an isometric view of a cabinet mounting bracket for mounting the cabinet shown in FIG. 2 in attached relation to a floor surface.
Figure 12:
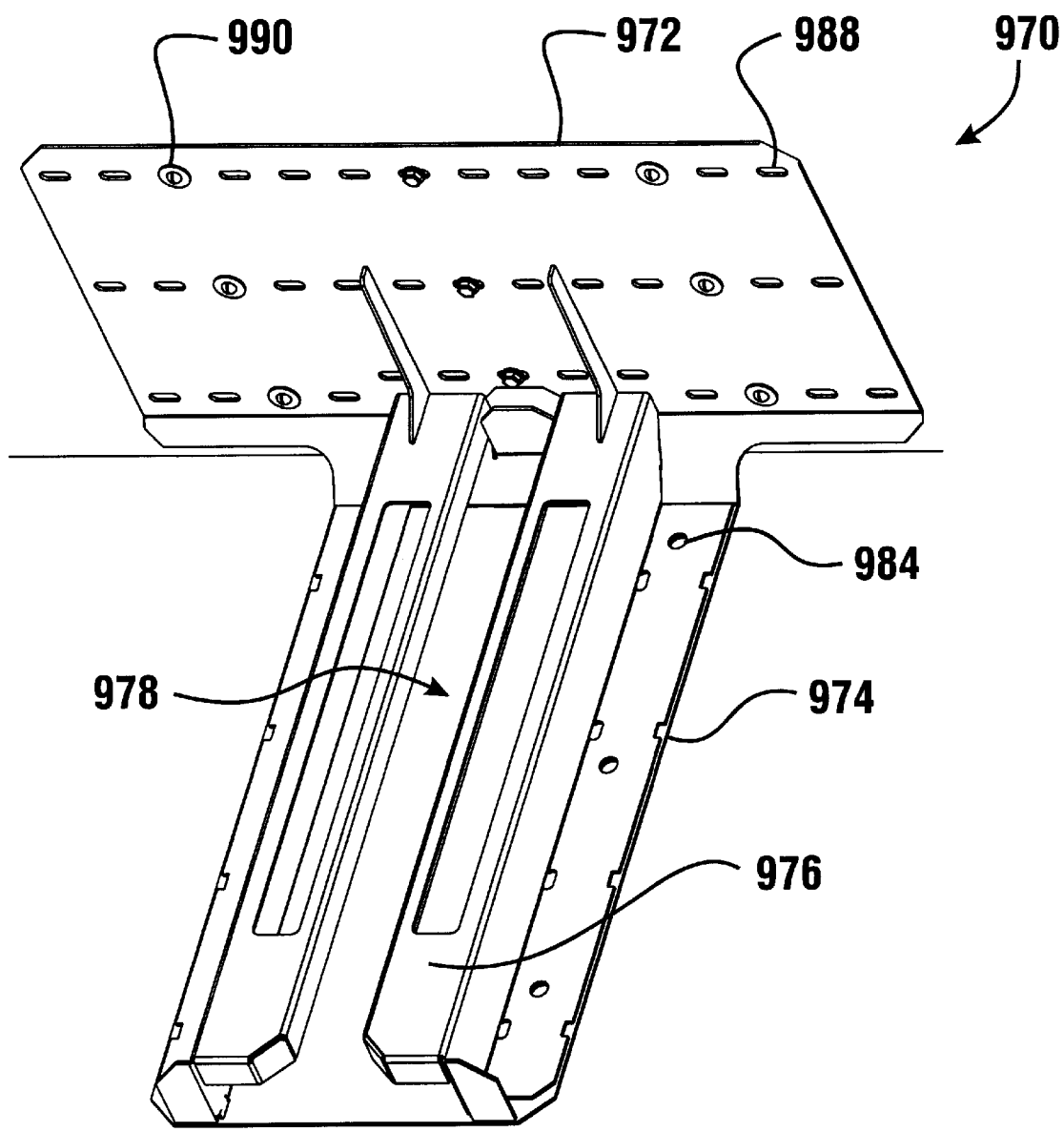
FIG. 12 is a view similar to FIG. 11 with the mounting bracket attached to a wall surface.

To reduce the risk of unwanted movement, cabinet 878 may be mounted using mounting fixture 970 shown in FIGS. 11 and 12. Mounting fixture 970 includes a vertically extending rear flange portion 972. Mounting fixture 970 further includes a lower flange portion 974. A pair of transversely spaced rails 976 extend above the lower flange portion 974. The rails 976 are transversely spaced from one another so as to provide a cross sectional T-shaped slot 978. The rails 976 are shown angled adjacent to the front entrance 980 to the T-shaped slot. Each of the rails 976 include an elongated slot 982, the purpose of which is later described in detail.

The mounting fixture 970 is adapted to be attached in fixed relation to an adjacent floor surface and/or wall surface. As best shown in FIG. 12, the lower flange portion 974 includes spaced apertures 984. As shown in FIG. 11, fasteners 986 may be extended through the apertures 984 to fasten the mounting fixture 970 to a floor surface.

The rear flange portion 972 in the described exemplary embodiment includes three rows of spaced apertures 988. Apertures 988 are spaced so that supports such as wall studs on various spacing can be engaged by extending fasteners such as fasteners 990 shown in FIG. 12, through the apertures. The slotted character of the apertures 988 in the exemplary embodiment facilitate anchoring the rear flange portion 972 to variously spaced wall studs which may be positioned in a wall behind the rear flange portion. Of course it should be understood that fasteners may be used to attach both the rear flange portion and the lower flange portion to adjacent supporting surfaces.

Figure 13:
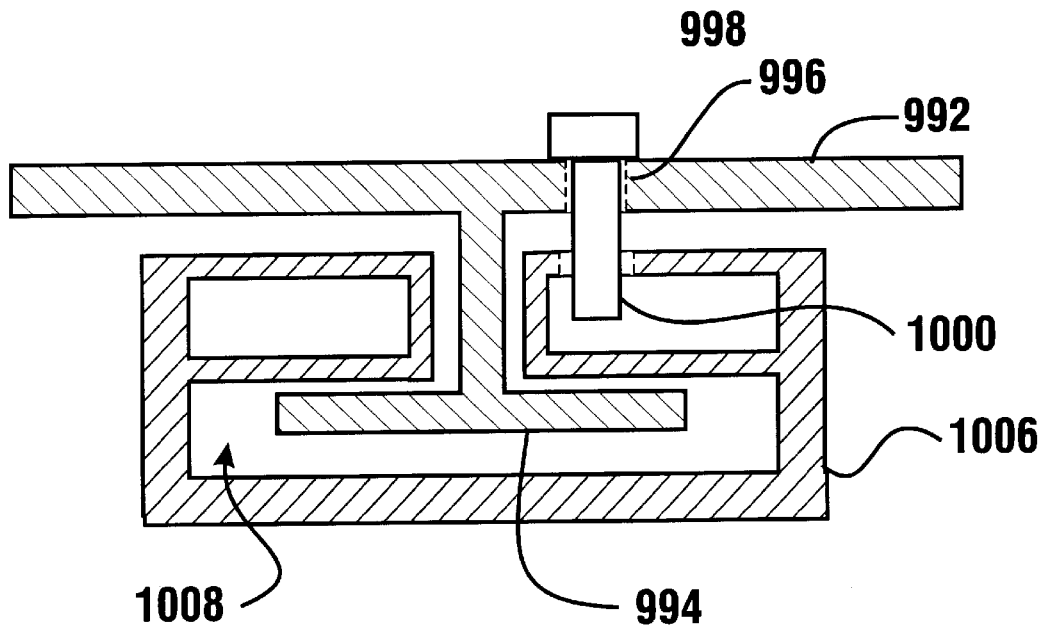
FIG. 13 is a cross-sectional view representative of how the bottom of the cabinet engages the mounting bracket.

In the exemplary embodiment, the housing 882 of cabinet 878 includes a lower wall portion 992. As shown in FIG. 13, lower wall portion 992 is in supporting connection with a generally T-shaped member portion 994. Member portion 994 is sized in cross section to be accepted into slot 978 of mounting fixture 970. As can be appreciated, member portion 994 can be guided into slot 978 through the entrance 980 which is facilitated by the cooperating angled surfaces on the outer end of rails 976.

With the member portion 994 extending in the slot 978, the rails 976 operate to hold the member and thus the cabinet in a generally horizontal position. This minimizes the risk that the cabinet will fall forward even if all the pullout shelves are fully extended.

As shown in FIG. 13, lower wall portion 992 includes at least one aperture 996 extending therethrough. A locking pin 998 or other fastener device or member may be extended through the aperture 996. A distal portion 1000 of a locking pin is operative to extend into the elongated slot 982 once the member 994 has moved substantially into slot 978. The engagement of the distal portion 1000 in the elongated slot 982 enables a cabinet to be moved forward until the distal portion engages the forward bounding surface of the associated elongated slot. This is useful as it allows a service person to move the cabinet away from an associated wall surface while still not operatively disengaging the cabinet from the mounting fixture. Such movement may be useful if one is attempting to access cables or other items which may extend behind the cabinet. Such movement may also be useful for purposes of accessing a lighting element for the interior of the cabinet.

Figure 17:
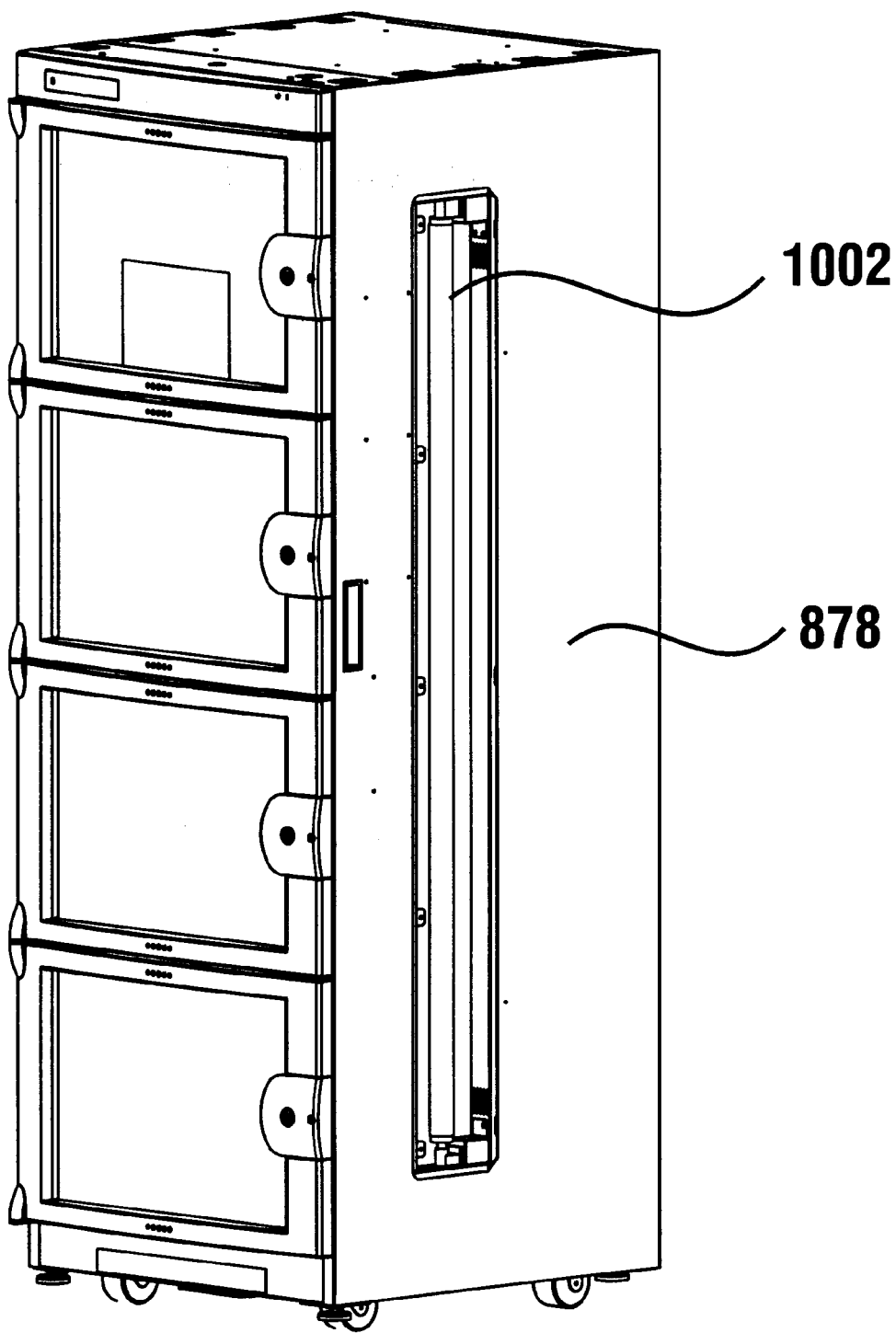
FIG. 17 is an isometric view of a supply cabinet showing a light access cavity including cabinet lights mounted therein.

As shown in FIG. 17, the light access door 900 on the side of the cabinet may be opened to access a tube light 1002. Tube light 1002 serves as a lighting element and is positioned behind a window which allows light to illuminate the interior area of the cabinet 878. As can be appreciated, if the side of the cabinet in which the light access door extends is adjacent to another cabinet or to a wall, the light access door could not be opened until the cabinet is moved sufficiently to provide access for the door to be opened. This may be achieved because the cabinet is moveable along the slot such that the cabinet may be moved forward sufficiently ahead of an adjacent cabinet to provide access sufficient to open the access door and change the tube light. Further, in the described embodiment, the transverse spacing between the rails 976 is sufficient so that the cabinet may be rotated to an extent which allows access to the light compartments or to other items which may be disposed toward one side of or toward the rear of the cabinet. This capability enables working on the cabinet while reducing the risk of disengaging the cabinet from the mounting fixture and causing potential tipping.

It should also be pointed out that the construction of the exemplary form of the cabinet 878 is also useful in that it enables changing the light tube 1002 by persons who do not have access to the interior area 884 of the cabinet. This enables the light tube to be changed by electrical workers or others who need not be provided access to the medical items housed within the cabinet. This avoids time consuming security procedures and observation of service personnel that would otherwise be required if the lighting apparatus were only accessible in the interior cabinet area A fixture indicated 1004 and shown in FIG. 14 may be used in connection with cabinets of the exemplary embodiment. Fixture 1004 includes an elongated portion 1006. Elongated portion 1006 has a structure generally similar to the rails of the mounting fixture 970. Elongated portion 1006 includes a generally T-shaped slot 1008. Slot 1008 is sized to accept member portion 994 therein. Elongated portion 1006 further includes an aperture 1010 therein. Aperture 1010 is sized to accept the distal portion 1000 of pin 998 or other fastening device.

Figure 14:
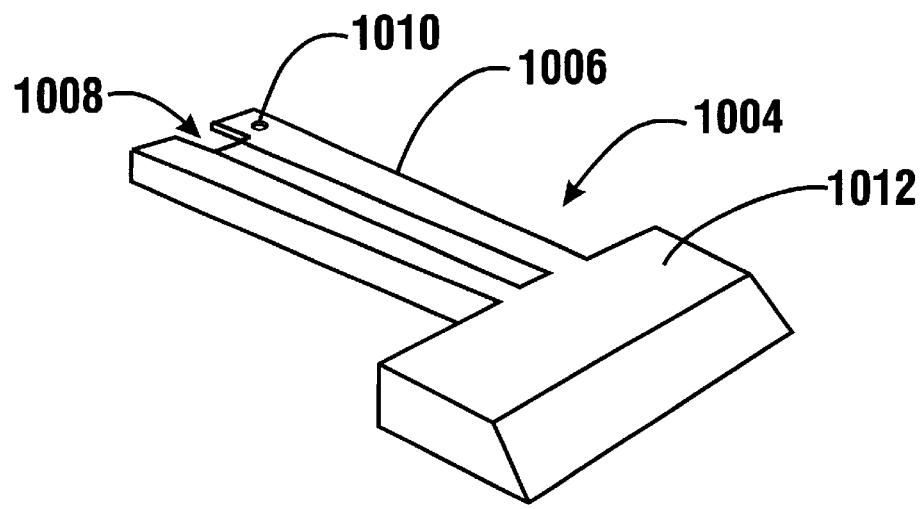
FIG. 14 is an isometric view of an anti-tip fixture for the supply cabinet shown in FIG. 2.

Fixture 1004 further includes an enlarged portion 1012 attached to the elongated portion 1006. As shown in FIG. 14, enlarged portion 1012 is substantially wider than the elongated portion and is of a sufficient length to provide enhanced resistance to tipping of the cabinet.

Figure 15:
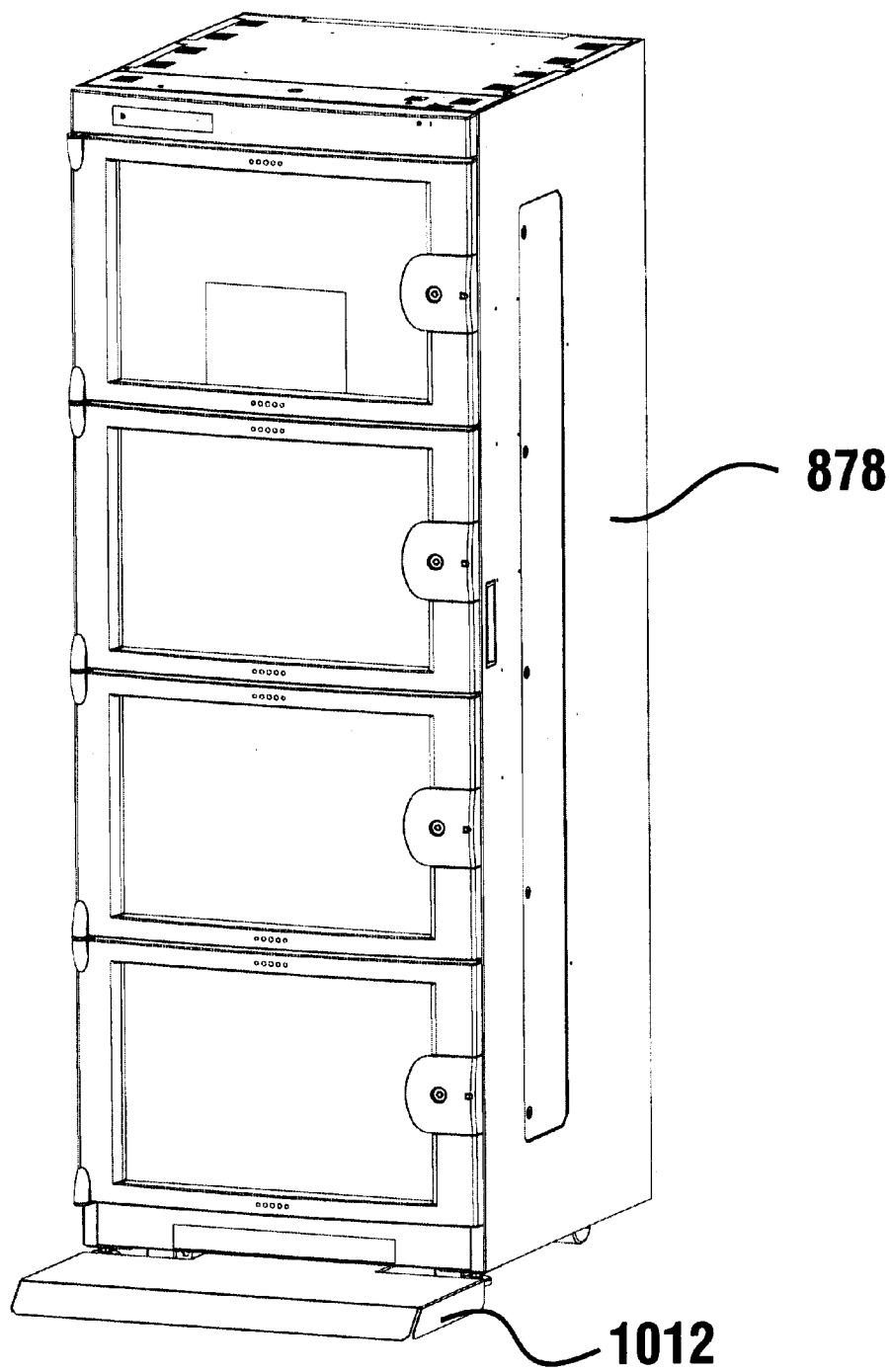
FIG. 15 is a front isometric view showing the cabinet of FIG. 2 engaged with the anti-tip fixture.
Figure 16:
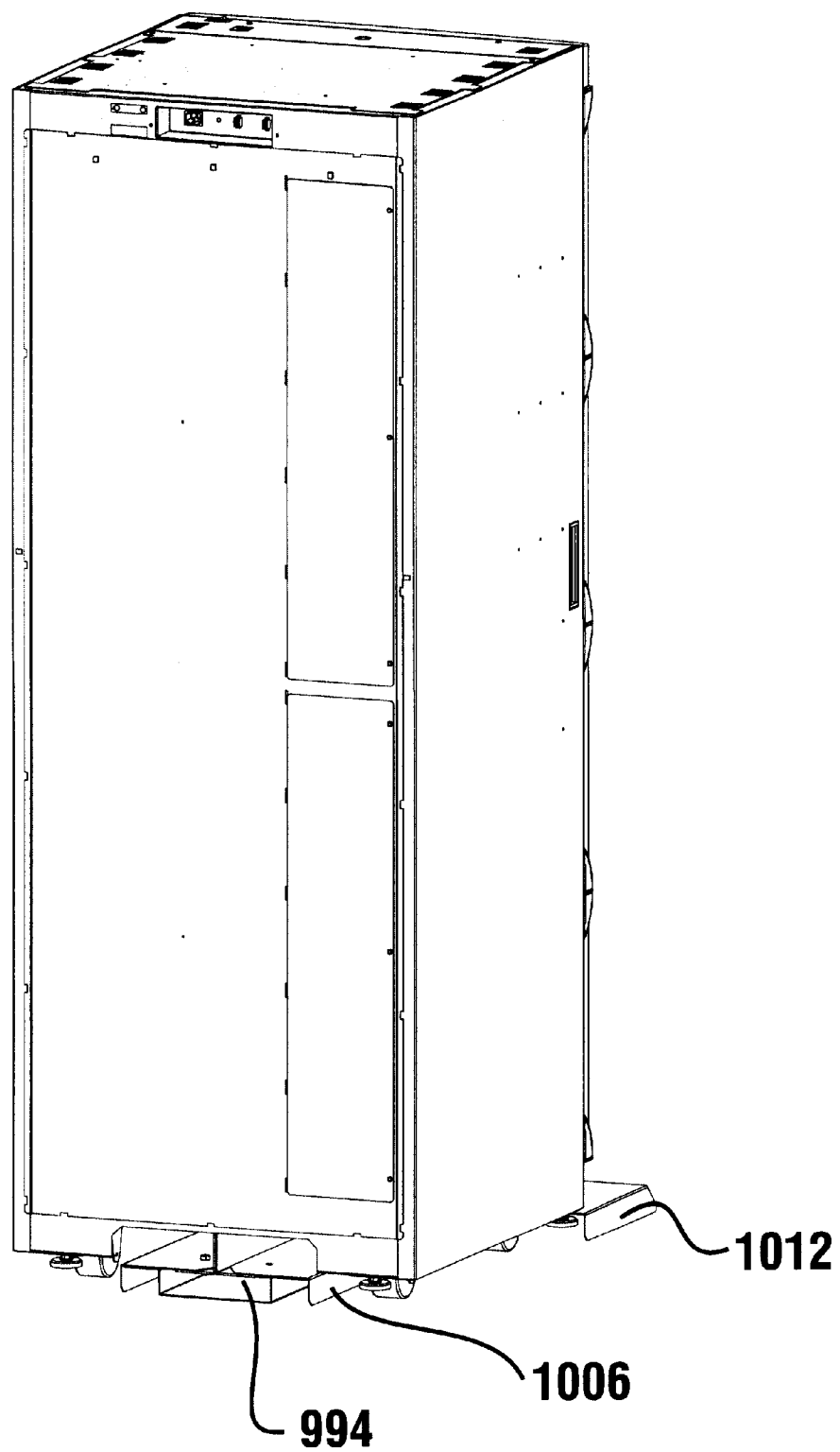
FIG. 16 is a rear isometric view of the cabinet and anti-tip fixture shown in FIG. 15.

Fixture 1004 may be used to minimize the risk of tipping of the cabinet 878 when the cabinet is not engaged with a mounting fixture 970. This may be useful, for example, when the cabinet is being worked on to install shelves or to load materials therein. To install the fixture, the member portion 994 is extended into the slot 1008. The pin 998 is extended through the lower wall portion of the cabinet such that the distal portion 1000 extends in the aperture 1010. With the fixture in this position, the enlarged portion 1012 extends forward of the front of the cabinet as shown in FIGS. 15 and 16. As a result, if the doors are opened and pullout shelves extended, the fixture tends to resist tipping movement of the cabinet in a forward direction. The construction of the fixture 1004 is such that a worker is enabled to readily work in and around the cabinet while it is engaged to the fixture without being hampered thereby. When the work activity is completed, the cabinet doors may be, closed and the cabinet moved on its casters or otherwise to a desired position where it may be engaged with a mounting fixture 970. Of course it should be understood that this arrangement is exemplary and in other embodiments of the invention, other approaches may be used.

Figure 18:
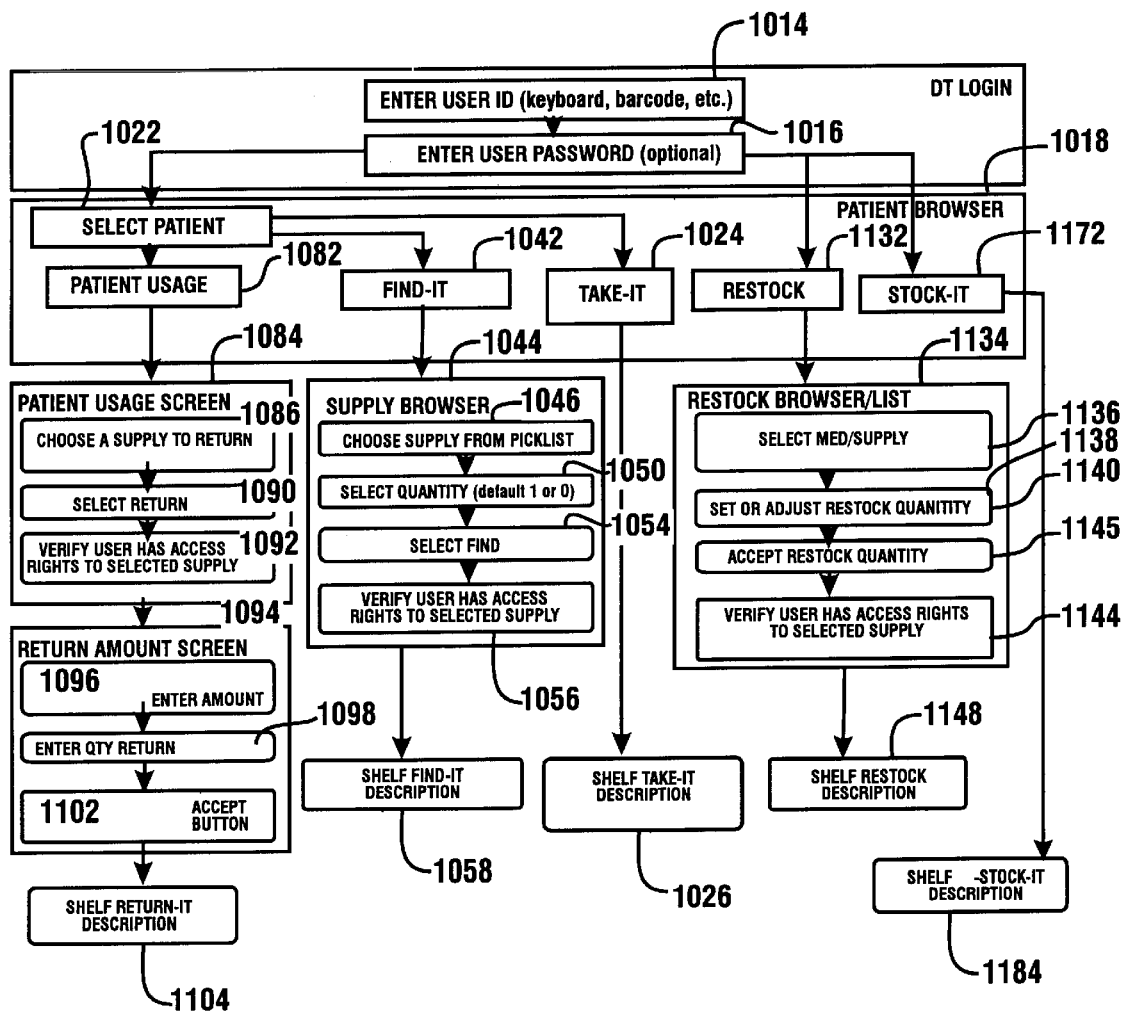
FIG. 18 is a schematic flow diagram showing exemplary operations that are carried out through a system including a display terminal in operative connection with the supply cabinet shown in FIG. 2.

FIG. 18 schematically indicates exemplary logic that is carried out in connection with a display terminal or other computer that controls operation of the supply cabinet 878. In a first step 1014, the user identifies himself to the system so that the system may verify that he is an authorized user. This can be done in any number of ways such as swiping a card which identifies the user, reading the bar code or other machine readable indicia on a badge or other article carried by the user, or inputting identifying information through an input device such as a keyboard. Alternatively, the user may be identified by biometric features such as appearance, voice, iris scan, fingerprint, or other similar feature that identifies the user as an authorized user of the system. In addition, some systems may include a requirement for a user to enter a password either orally or through a keyboard to further verify that the user is an authorized user. This is represented by a step 1016. In response to the input by the user of identifying information, the computer holding data representative of authorized users determines if the inputs correspond to an authorized user. If so, the system operates to enable the user to proceed to carry out further steps. Of course if the information input does not correspond to that of an authorized user, further access is denied.

Figure 23:
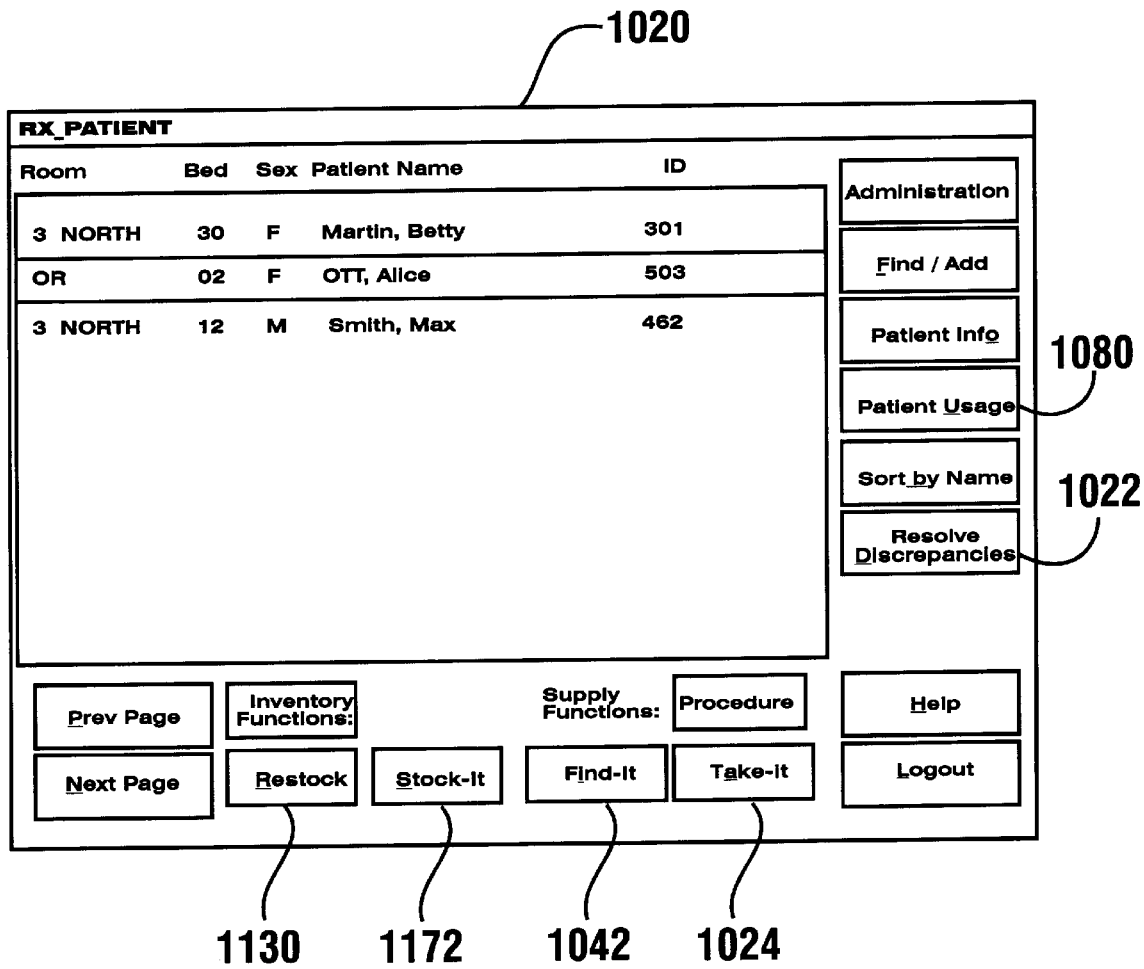
Figure 28:
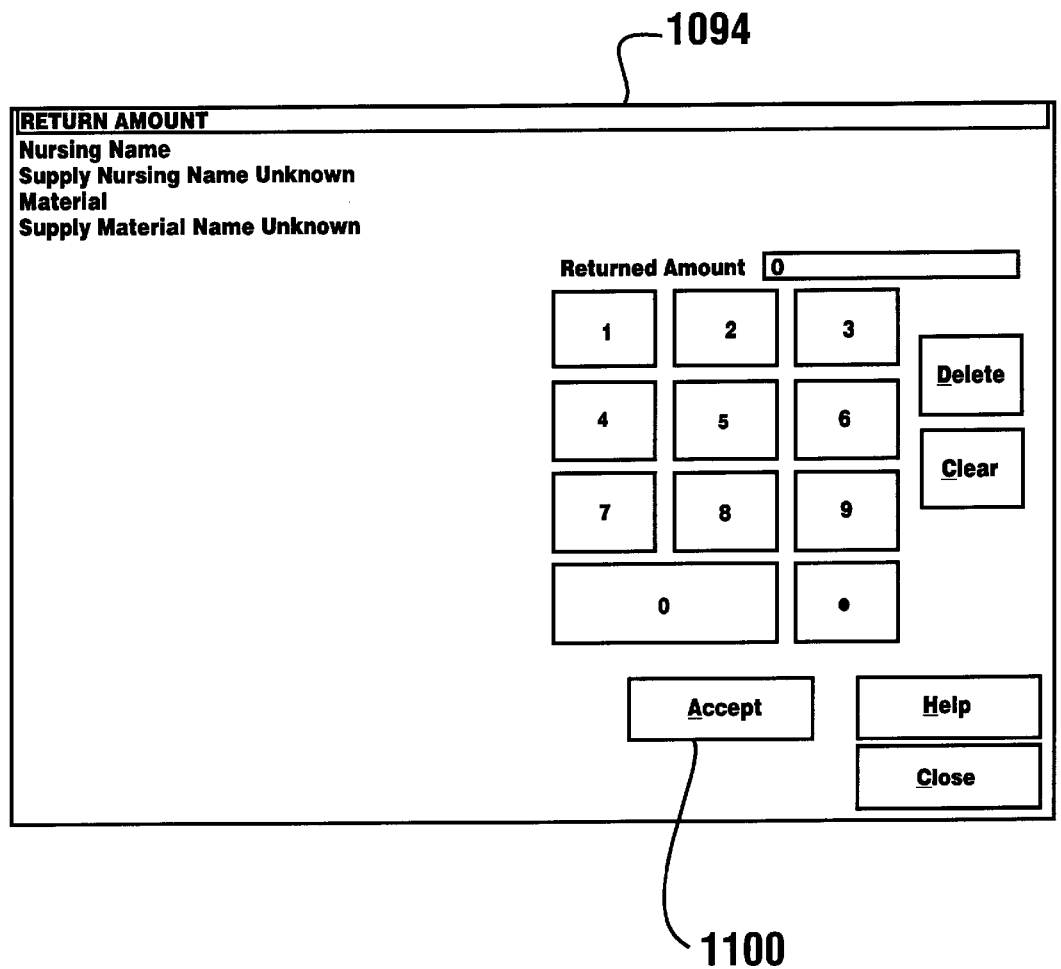

Once the user is determined to be an authorized user, the computer operates in a step 1018 to cause a patient browser screen to be displayed on the display terminal. In the exemplary embodiment, the patient browser screen is screen 1020 shown in FIG. 23. Screen 1020 is generally similar to the patient browser screen 222 shown in FIG. 28 of the incorporated disclosure of U.S. Pat. No. 5,912,818. Patient browser screen 1020 includes many of the same icons as screen 222 and additional icons relating to operation of the cabinet as later described.

From the patient browser screen, as represented in FIG. 18, a user is enabled to select a particular patient by providing an input in a step 1022. This is done in the described embodiment through the touch screen by the user bringing a finger adjacent to the displayed name of a patient of interest. Upon doing this, the system is operative to cause the name of the patient to be highlighted. This activity further causes the computer to operate so that the records associated with that particular patient are modified based on further inputs provided to the system.

Upon selecting a particular patient, the user then has several options for activities that may be performed. In situations where the user knows what it is that they need from the cabinet or a group of cabinets for the particular patient, the user can select a "take it" button 1024 from the patient browser screen 1020. This is done by the user providing an input by bringing their finger adjacent to the take it button on the touch screen of the display terminal. In response to the user activating the take it button, the computer is operative to carry out a series of steps 1026.

Figure 19:
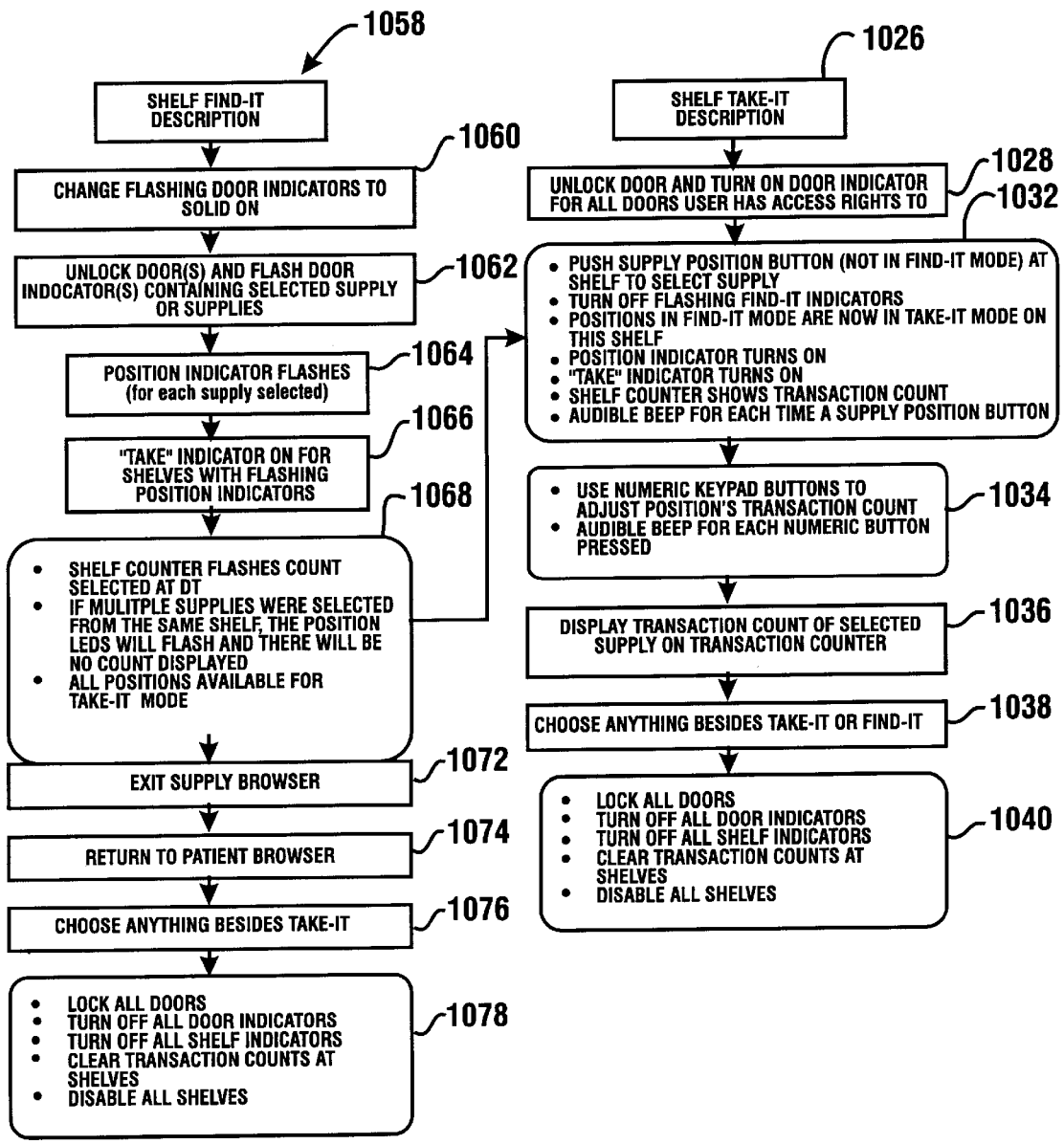
FIGS. 19–22 are flow charts showing exemplary functions carried out through a system including a display terminal in operative connection with the supply cabinet shown in FIG. 2.

The exemplary series of steps 1026 that are carried out in connection with the take it option is shown in FIG. 19. In response to selection of the take it button 1024, the computer is operative in a step 1028 to open all of the doors of the cabinet to which the user has access rights. This is based on data stored in one or more data stores concerning the medical items stored in storage locations behind the doors, and stored information concerning the authority of the user to have access thereto. In step 1028, each of the doors holding such items is opened in response to signals from the display terminal that open the electronic locking mechanisms of the doors. In addition, the indicator light associated with each of the doors that have been unlocked is actuated. In the exemplary embodiment, the medical items are stored in the locations such that they are arranged in categories so that no medical items are accessible to a user when a door is unlocked that the particular user is not authorized to have access to.

Figure 5:
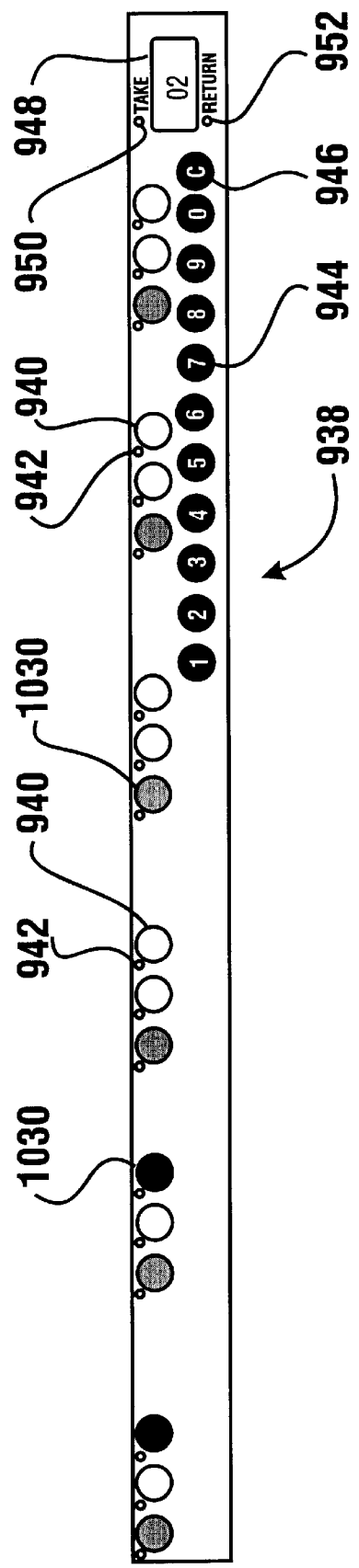
FIG. 5 is a plan view of an exemplary shelf interface.

Once the doors have been opened, the user indicates the position of the medical item that they intend to take by pressing a particular button corresponding to the storage location holding the medical item on the corresponding shelf interface 938. As represented in FIG. 5, buttons 940 which are associated with medical items in the exemplary embodiment have applied thereto a self adhesive label. This self adhesive label is preferably an indicator as to the particular button that is active and distinguishes the button from others which may not be associated with the medical item. Further, in embodiments of the invention, the label that is applied to active buttons is correlation coded with a storage location through visible indicia such as through a color code. Labels or other indicators of a corresponding type, such as a label having the same color, may be placed or applied in storage locations to which the button corresponds. In this way, a user is enabled to correlate a particular button with the storage location for a particular medical item by correlating the color label on the button to the color label in the storage location. In FIG. 5, color labels on selected ones of buttons 940 are indicated 1030. In situations such as with pullout shelves, each of the active buttons 940 on a particular shelf interface may have a different color. Of course it should be understood that in situations such as with stationary shelves where there may be a small number of medical item types or perhaps only even one item, it may not be necessary to color code the particular storage locations and it would be sufficient to apply a color label 1030 to the active button(s) to indicate which of the buttons are operative. This feature enables a common shelf interface to be used with various shelves and with various numbers and arrangements of storage locations. It should be understood, however, that the use of color coding is exemplary and in other embodiments, other types of approaches to correlating buttons or other indicators and storage locations may be used.

Returning to the description of the "take it" operation in FIG. 19, the user touches the corresponding button 940 for the medical item being taken in a step 1032. In response to the particular button being pressed, the associated indicator 942 is illuminated on the shelf interface. The user then inputs through the numeric keypad 944 a particular number corresponding to the quantity of that type medical item being taken. The user does this by pressing the numerical indicators comprising the keypad. As this is done, the number selected is displayed as a numeral through the interface display 948. If the user makes a mistake in inputting the type or number of items taken, the user can clear the incorrect input by pressing the "clear" button 946. This is done in a step 1034. As the user selects the button for a particular medical item and provides numerical inputs, the type of medical item selected and the quantity indicated as being taken is displayed on the screen of the display terminal. This is represented in a step 1036. Once the user has selected a particular medical item from one storage location, the user may take a different type of medical item from the same shelf or from a different shelf to which they have access. In doing this, the process described of touching the associated button and providing the numerical input through the keypad is repeated. As the user selects items in this manner, one or more connected computers, such as the display terminal, operate at that time or at a later time to record the taking of these medical items for the particular patient selected in at least one data store.

When the user has completed the activity of taking items for the patient, the user may make another selection or provide another form of exit input to the display terminal to close the series of steps associated with taking items for the patient. This is reflected in FIG. 19 in a step 1038. In response to such action, the display terminal or other computer operates in a step 1040 in the exemplary embodiment to lock the doors, clear the shelf indicators and to return to a ready state.

In some circumstances, a particular user may not know exactly where items that are required for a patient are located among storage locations in one or more cabinets. In these circumstances, the system of the exemplary embodiment enables a user to locate a particular item. This is done by the user selecting the patient in the patient browser screen 1020 and then providing an input selecting the "find it" button 1042. As represented in FIG. 18, in the exemplary embodiment selection of the find it button causes the computer to operate to display a supply browser screen 1044 shown in FIG. 24. A supply browser screen is generally similar to screen 264 shown in FIG. 32 of incorporated U.S. Pat. No. 5,912,818 and operates in a generally similar manner.

As represented in FIG. 18, when presented with the supply browser screen 1044, a user is presented with a listing of supplies. The user selects the desired supply from the list by proving an input that comprises touching the touch screen adjacent to the name of the particular medical item. This is represented by a step 1046. In some embodiments the user may then select the desired quantity of the particular item by inputting a quantity by touching a quantity button 1048 on screen 1044. In the exemplary form of the invention, the quantity is set to a default value. The default value may be preferably either a one (1) or a zero (0) depending on the programming of the particular system. The selection of a quantity is represented in FIG. 18 by a step 1050. In alternative embodiments the user may not be presented with the option of entering a quantity. This may be done for example where each shelf in the cabinet has an associated shelf interface and quantities other than the default value of one (1) must be conducted through a "take it" type transaction.

Figure 24:
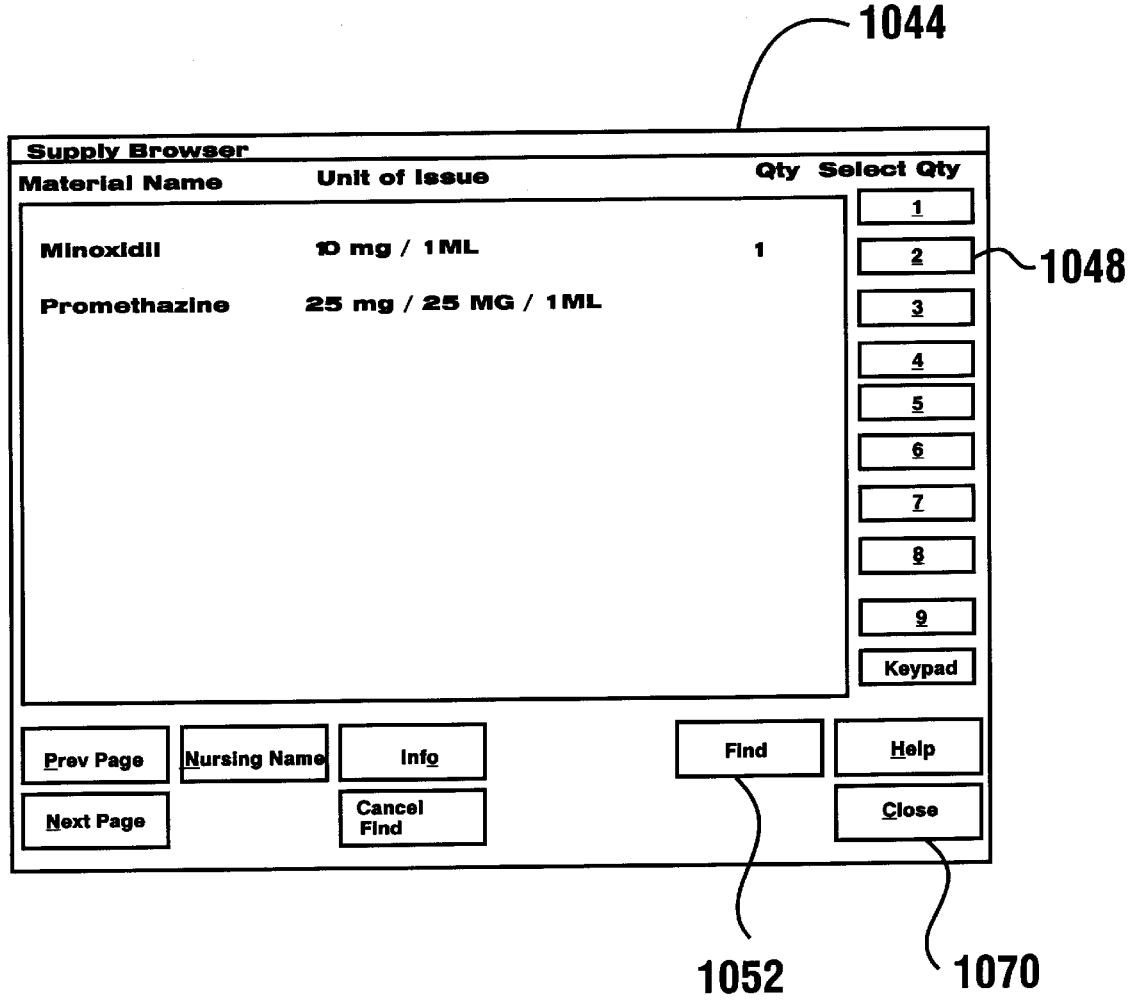

After the user has selected the particular item that they wish to take for the patient and the quantity (if required), the user is guided to the particular item in response to touching a "find" button 1052 shown in FIG. 24. This is represented by a step 1054 in FIG. 18.

In response to the user providing an input corresponding to touching the find button, the computer operates as indicated in FIG. 18 in a step 1056 to determine if the user has a right to access the particular medical item which they have selected. This is done by consulting data in at least one data store. If the computer determines that the user has such rights, the computer operates to execute a series of steps schematically indicated 1058. If the user does not have such rights an indication thereof is output to the user through the display terminal.

The series of steps executed by the computer in an exemplary "find it" operation are shown in FIG. 19. In response to the user selecting a particular item or one or more items, the indicators on the doors controlling access to the shelves holding such items are illuminated and the locks holding such doors in a closed position are caused to be electronically unlocked. This is represented in FIG. 19 by steps 1060 and 1062.

At the same time that the doors are unlocked, the indicator 942 adjacent to the particular button(s) 940 with which the storage location for each selected medical item(s) is activated by being turned on so as to guide the user to the particular location holding each selected item. This is represented in FIG. 19 by a step 1064. At the same time, the take indicator 950 on the shelf interface from which an item is to be taken is illuminated. This is represented in FIG. 19 by a step 1066. The display 948 may also display the particular quantity of the medical item from the particular shelf that was selected through the inputs to the display terminal or the default value in systems where no input is provided. However in an exemplary embodiment, if multiple items have been selected and at least two of those items are located on the same shelf, the display on that shelf does not indicate a number initially. In the described exemplary embodiment the user, if they do not recall how many of a particular item were requested, may review the supply browser-screen on the display terminal. Alternatively in some embodiments, a user can obtain the quantity of a particular item selected by touching the associated button. This causes the number corresponding: to the quantity selected to be displayed on the display 948. This is represented in FIG. 19 in a step 1068. Of course in other embodiments other approaches may be used such as cyclically displaying quantities selected with corresponding illumination of position indicators on a shelf interface. In cases where only one item from a shelf has been selected the indicator and quantity for that item may be indicated continuously. Other ways of indicating positions and quantities through a shelf interface will be apparent from the description. provided herein.

On occasion, a user who is operating the system in a "find it" operation may determine that they wish to take additional items or quantities that they did not select at the display terminal when selecting medical items. If this occurs in the exemplary embodiment, the user is able to indicate the taking of additional items in a manner similar to that done in the "take it" mode previously described. This is represented in FIG. 19 by the logical connection between step 1068 and step 1032 in the take it operation. In this way, the user is enabled to take whatever medical items they may wish to take from the cabinet through touching multiple buttons and inputting quantities selected.

Assuming the user only is taking the items that were originally selected through the display terminal, the user can end the operation by providing an exit input through selecting the close button 1070 in the supply browser screen 1044. This is indicated in FIG. 19 in a step 1072. This causes the system to return the display terminal to the patient browser screen 1020. This is represented in FIG. 19 by a step 1074. If the user provides certain inputs to the system other than those associated with a take it operation as represented in a step 1076, the system operates in a step 1078 to close the transaction. This is done by generating signals that are operative to lock all the doors, turn off the shelf indicators and door indicators, clear the transaction counts of the shelves, and disable the associated shelf interfaces. The data concerning the medical items removed from storage is also stored in a data store. As can be appreciated, the exemplary form of the invention enables a user to have the benefit of locating medical items through inputs that guide the user to the particular storage location. However, the user once access has been provided to the cabinet interior and upon determining that additional items are needed, is provided with the capability of indicating what is to be taken through inputs to the shelf interface. This is often a useful, timesaving feature in certain circumstances. It should be understood however, that in other embodiments, other approaches may be used.

In the described embodiment of the system, the user is also enabled to return items to storage that were previously taken for a patient and not used. As represented in FIG. 18, to return an item, a user first logs into the system to identify himself as an authorized user through steps 1014 and 1016 previously described. The user then operates to select the particular patient for which an item is being returned through the patient browser screen 1020 and selecting a particular patient as was previously discussed in connection with step 1022. On the patient browser screen, a user may then select a patient usage button 1080 through the touch screen. This is represented by a step 1082 in FIG. 18.

Figure 30:
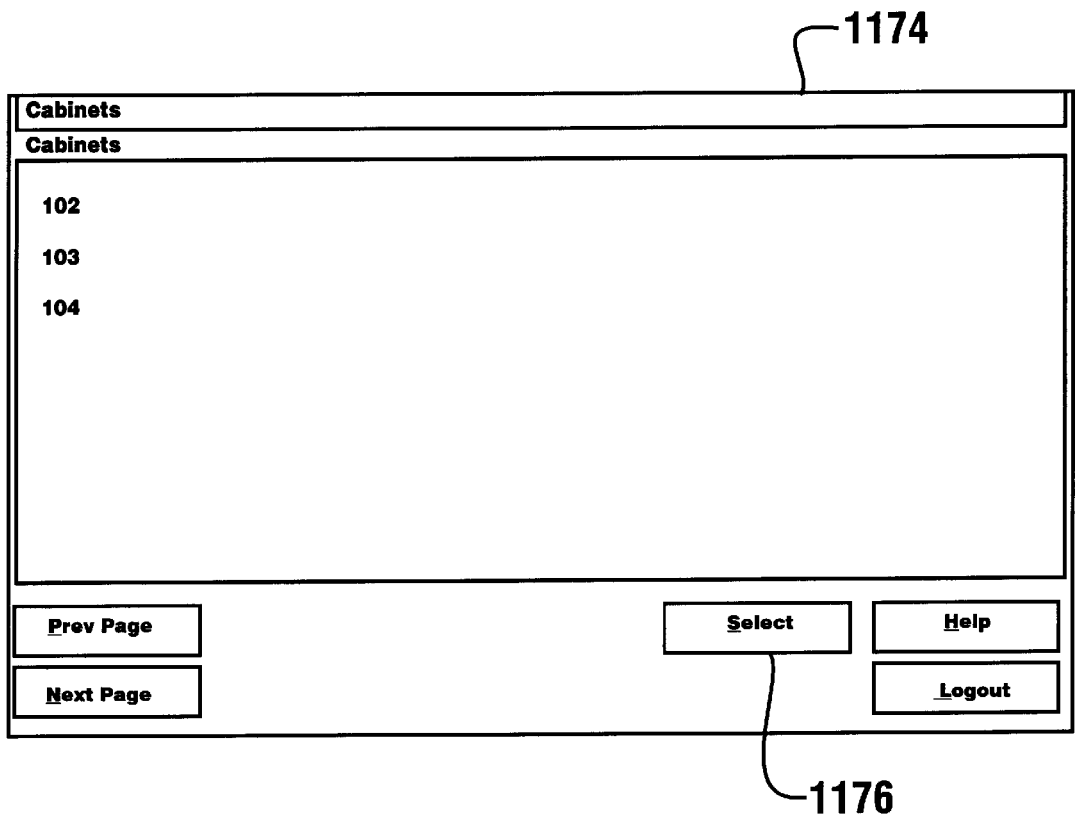

In response to selecting the patient usage button, a patient usage screen is displayed at the display terminal. The patient usage screen is generally similar to screen 244 shown in FIG. 30 of the incorporated U.S. Pat. No. 5,912,818. In the described embodiment, the patient usage screen has a slightly different format shown by screen 1084 shown in FIG. 28. The patient usage screen indicates items that have been taken for a patient. Generally, this will include a plurality of items and the information related thereto.

A user wishing to return a medical item highlights the particular supply to be returned by touching the touch screen adjacent to the particular item. This is represented in FIG. 18 by a step 1086. After selecting the particular item, the user may indicate that they are returning the item by touching the return button 1088 in FIG. 28. This is represented by a step 1090 in FIG. 18.

In response to the user indicating that they are returning an item, the system operates in a step 1092 in a manner like that already discussed to determine if the user has authority to access the particular storage location and/or the group of locations that will be made accessible to the user if the item is returned to its proper storage location.

Figure 29:
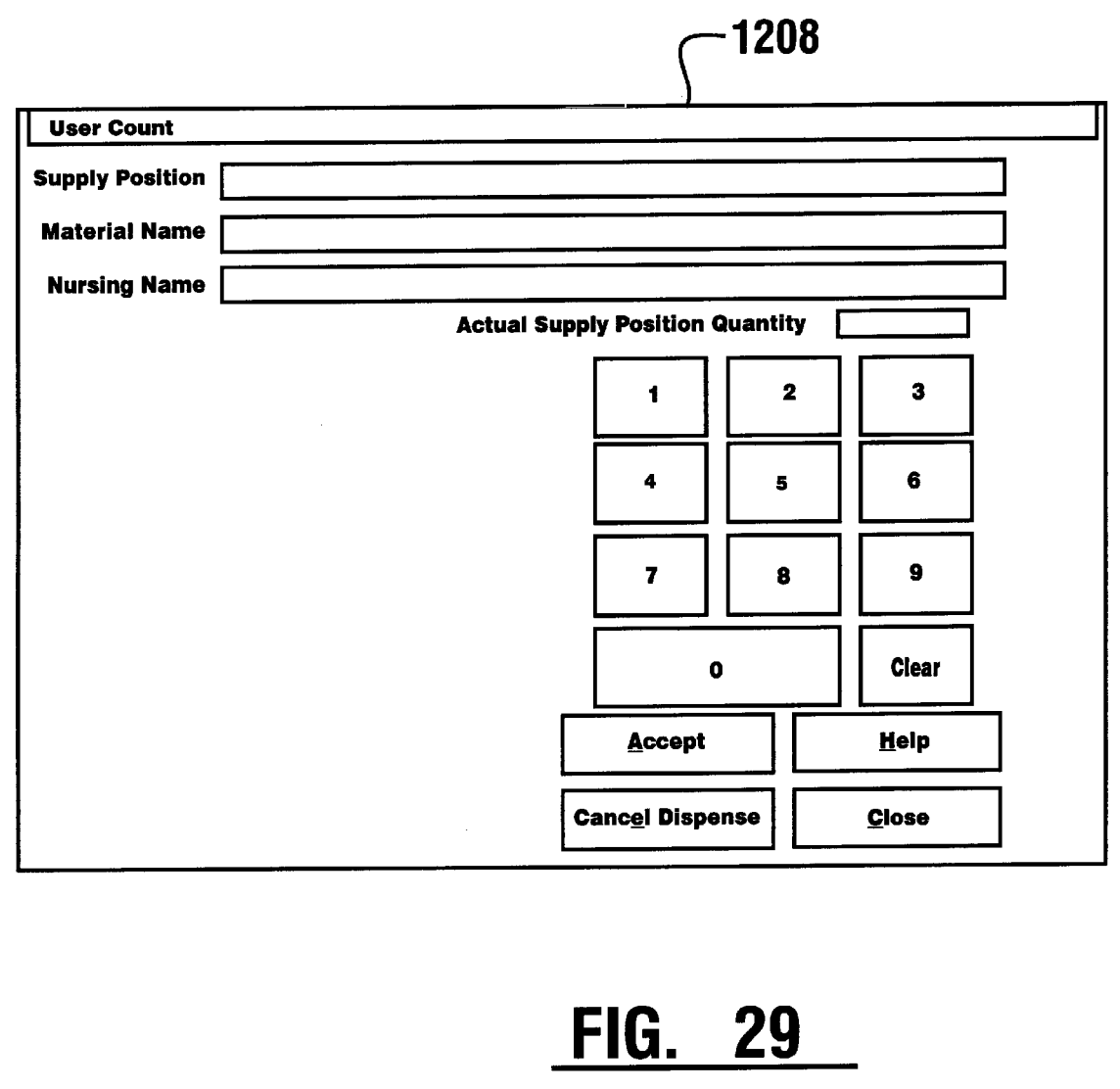

If the user is authorized to have access to the particular location, the user is presented with a return amount screen 1094 having the layout shown in FIG. 29. On the return amount screen, the user is enabled to select or otherwise input to the system an amount of the supply being returned. This is indicated by a step 1096 in FIG. 18.

The user enters the amount being returned through inputs generated by touching buttons generated on the screen 1094. This is represented in FIG. 18 by a step 1098. Once the user has properly entered the amount of the return, the user can indicate that the information is correct by pressing the accept button 1100. This is represented in FIG. 18 by a step 1102. Of course, if the user makes an error in inputting the information, they can change the inputs through the use of "delete" and "clear" buttons on screen 1094. In addition, if a user determines that they are not going to return a particular item, they may select the "close" button and return to a prior screen.

Figure 20:
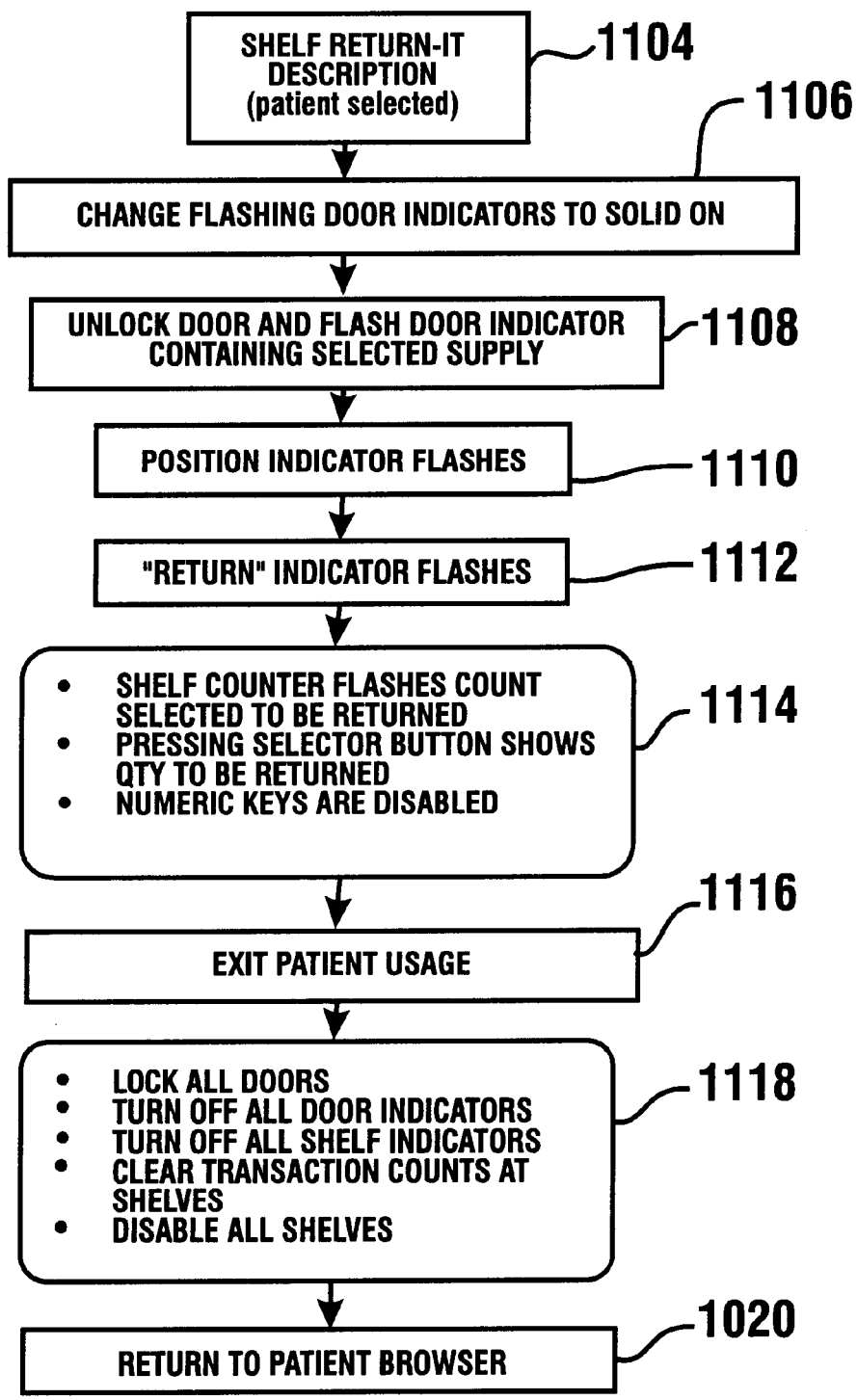

After the user has touched the "accept" button in step 1102, the computer is operative to execute a series of steps 1104. The series of steps 1104 is represented in FIG. 20. The display terminal operates to make the particular storage location for the item to be returned accessible to the user and to guide the user to the particular location. This is done by illuminating the indicator for the particular door holding the storage location for the type of item being returned in a step 1106 while the door is unlocked in a step 1108. Simultaneously, the indicator 942 associated with the button that can be visually correlated with the storage position is illuminated on the particular shelf interface to which the item is to be returned. This is represented by step 1110. Also, the return indicator 952 indicating that an amount is being returned to the shelf is illuminated as indicated by a step 1112. The display 948 on a particular shelf interface shows the particular quantity number to be returned as represented in a step 1114. However, in the exemplary embodiment in circumstances where a number of items have been identified to be returned, and two or more items are positioned on the same shelf, the position indicators 942 will illuminate but the display will not indicate the particular number to be returned. A user can be reminded of a number to be returned to a particular location by touching the button associated with each activated indicator. Doing this causes the display to output the number to be returned to each particular storage location. In this way, a user can be reminded of items to be replaced in each storage location on each shelf. Of course in other embodiments other approaches may be used.

The user may end the return operation by touching the close indicator as represented in a step 1116. This causes the display terminal to return all the doors to the locked condition and to turn off the indicators on the shelves as represented in a step 1118. The information concerning the return is stored in a data store. The system then operates in response to the programming of one or more processors in the display terminal to return the display terminal to the patient browser screen as represented in a step 1020.

The described exemplary system also facilitates restocking of the system. As represented in FIG. 18, a restocking user must first identify himself to the system through steps 1014 and 1016 in the manner previously described. This then causes the execution of step 1018 which presents the patient browser screen 1020 shown in FIG. 23. From the presentation of the patient browser screen, a restocking user may select a restock button 1130 which causes the display terminal to execute the step represented 1132 in FIG. 18 which causes a restock browser list to be displayed at the display terminal.

An exemplary format of the restock browser screen 1134 is shown in FIG. 25. Although screen 1134 does not show a listing of positions and material names, it should be understood that such data will be displayed corresponding to some or all positions in which items are stored in the cabinets. A user is enabled to page through the listing of items in the cabinets by using the "previous page" and "next page" buttons in screen 1134.

The user is enabled to select a displayed supply name by providing an input by bringing a finger adjacent to the supply name on the screen and then selecting the select button 1135. This is represented in FIG. 18 by a step 1136. The display terminal then operates to cause a stock amount screen 1138 having the format shown in FIG. 26 to be displayed. It should be understood that the stock amount screen will include the information for the particular medical item in the position selected. While the stock amount screen 1138 is displayed; a user can select the restock quantity button 1142. Then, a user is enabled to input a restock quantity through the numeric keys on a keypad display 1139 therein. This is represented in FIG. 18 by a step 1140.

Once the user has input the restock quantity through numeric inputs through the keypad display 1139 the display terminal in response to screen 1138, the user can indicate that they are ready to restock that quantity by-touching an accept button 1143 from screen 1138. This is indicated at a step 1145. Of course as can be appreciated, the system functions associated with screen 1138 also facilitates restocking by enabling the restocking user to touch an icon indicating restocking a maximum amount. The user is also enabled to unload items that are stored so as, for example, to make room for additional items by indicating an unload quantity related to the storage location. Buttons are also provided so that a quantity of expired items can be indicated as removed.

Also, if there are any discrepancies, a discrepancy button is provided which generates a discrepancy screen enabling the user to indicate any discrepancies to the system and have the information stored in a data store. Screen 1208, having the format shown in FIG. 29 may be used to input the actual number of items received when the number recorded as taken within the system does not reflect that which was actually taken. Screen 1208, populated with data and having the format shown in FIG. 29 is operative to indicate the remaining quantity of items after the taking operation has occurred. This enables a user to indicate any discrepancy related to the number of items that are observed as remaining in a particular storage location as compared to that which the system indicates as remaining after a find it or take it transaction. The data input in response to each screen is stored in a data store it should be understood that these screens are exemplary and in other embodiments of the invention, other or additional types of interfaces and optional inputs may be provided for capturing such information in the system.

In response to selecting the accept button 1143 as represented in a step 1144 in FIG. 18, the connected processors in the system operate to determine if the user has rights to access the particular storage location that they are indicating that the user is planning to restock. If the user has authority to restock the particular storage location, the system operates to execute a series of steps 1148 that are shown in greater detail in FIG. 21.

In response to the restock indication being given, the computer operates to indicate the door behind which the particular storage location is located for the item to be restocked as indicated in a step 1150. This is done by a processor operating to activate the appropriate door indicator. The particular door or doors if multiple items are being returned, are unlocked as indicated in a step 1152. The display terminal further operates in accordance with its programming to place the shelves in a restock mode in a step 1154 and the indicators 942 associated with the buttons for the particular locations indicated as being restocked are illuminated in a step 1156.

As indicated in a step 1158, if only a single storage location on a shelf is being restocked, the number on display 948 will indicate the number of the particular item to be stocked and the corresponding indicator will be illuminated on the shelf. If multiple items are returned to a particular shelf, the display does not indicate a number until a corresponding button adjacent to an illuminated storage position indicator is pressed. When this occurs, the display indicates the number to be restocked into that particular location. This is represented in a step 1160.

Figure 21:
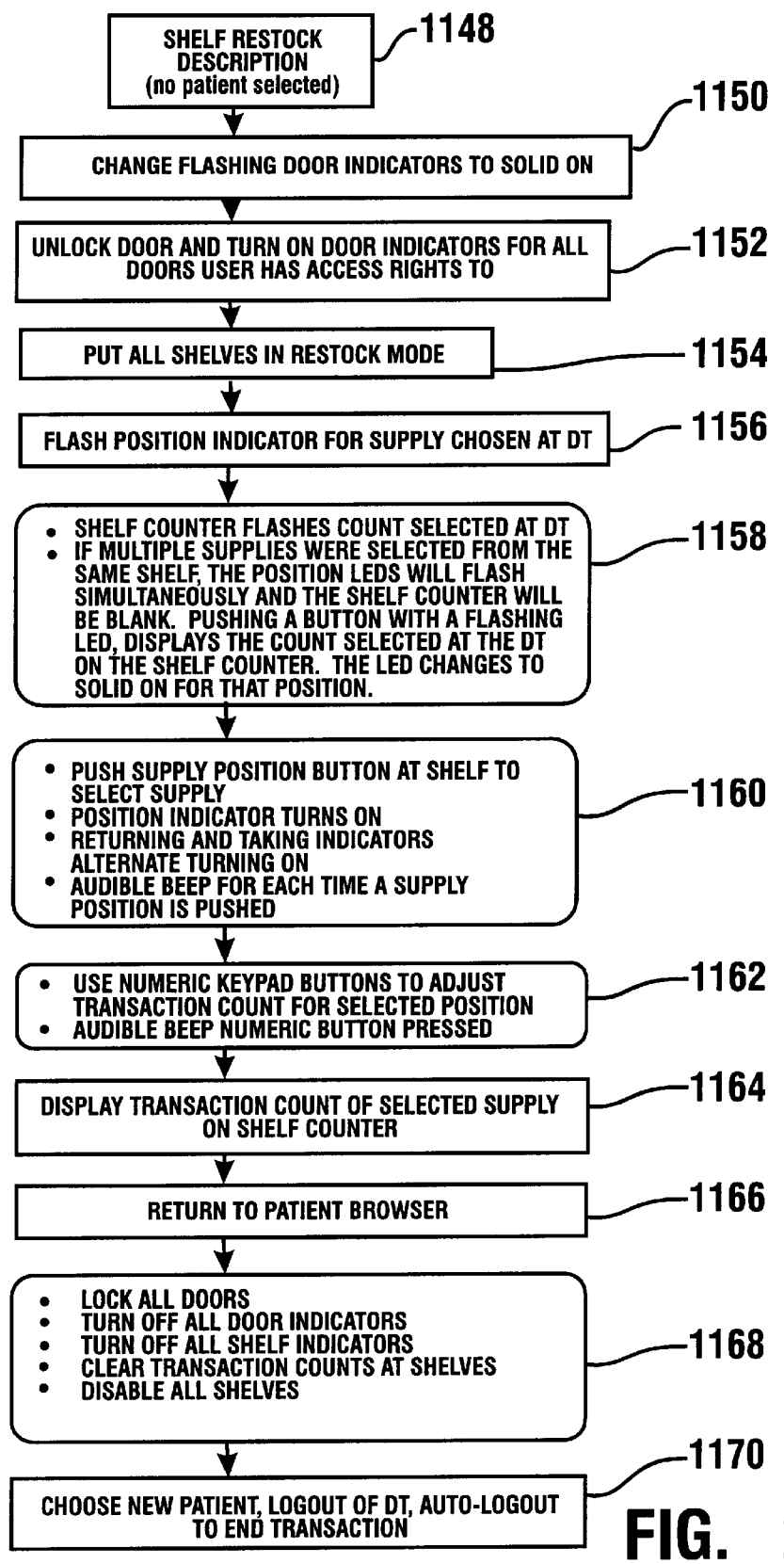

If in the restocking activity it is determined that the quantity to be restocked that has been input at the display terminal was incorrect or if there is a need to restock in additional locations, a user can press a location button 940 and indicate a different quantity to be input through the numerical keypad 944. The count of items is also correspondingly adjusted at the display terminal. This is represented in FIG. 21 by steps 1162 and 1164. When the user has completed the restocking activity, the user may touch the "close" button in the restocking browser screen that causes the display terminal to return to the patient browser screen as represented in a step 1166. At the same time, the display terminal operates to lock all the doors, turn off the indicators and clear shelf interfaces as represented in a step 1168. The data in the data store is also updated. Thereafter, the user may operate the system to choose a new patient, to log out, or the system may automatically log the user out after a timeout period. This is represented in FIG. 21 by a step 1170. Of course it should be understood that these stocking steps are exemplary and in other embodiments, other approaches may be used and options provided.

The described form of the invention further enables restocking of the cabinets in a predetermined manner based on a listing of restocking activities that has been compiled based on prior information and dispensing activities. For example, in some embodiments of the invention, the system may operate to generate a restocking report indicating locations where additional quantities of items are required. A selection of these items may then be compiled in the pharmacy or other location and transported to the particular area for restocking. Alternatively, a listing of such items may be compiled by computers operating in the system in response to a particular request input through the display terminal associated with the particular cabinet. In this way, restocking activities of a plurality of locations may be facilitated without the user having to input through the display terminal inputs corresponding to storage locations.

In the described exemplary embodiment, the stocking activity may be initiated after the user has logged onto the display terminal in the manner previously discussed by selecting a "stock it" button 1172 from the patient browser screen. This causes the processors connected in the system to generate or call up a restock report related to the cabinets associated with the display terminal. The display terminal then operates to display a cabinet selection screen indicated 1774 and which has the format shown in FIG. 30. The cabinet selection screen 1174 displays a listing of cabinets in connection with the display terminal. A user then highlights a particular cabinet to be restocked and touches a "select" button 1176 to select a particular cabinet that has been highlighted.

In response to selecting a particular cabinet, the system operates to cause a "stock it" screen 1178 having the format shown in FIG. 31 to be displayed on the display terminal. Stock it screen 1178 in embodiments of the invention may reflect the supply positions that are contained in the restock report. It should be understood that although the exemplary format of the stock it screen 1178 does not include this data, in operation when the data is available a listing of such positions and data will be included in the screen.

A user is enabled to find particular locations for items by providing an input. This is done by highlighting the item by touching a particular item listed in the screen 1178 and by touching a find button 1180. This causes the display terminal to operate to unlock the doors of the associated cabinet holding such items and to illuminate the location indicators for the buttons that are associated therewith. A restocking user is enabled to locate the particular locations and input the additional items to each as indicated both on the screen 1178 as well as on the display 948 of the shelf interface. A user is enabled to indicate that they have restocked the particular position by touching the accept button 1182 on screen 1178. Touching the accept button will indicate that the particular position or positions have been restocked to the levels desired as indicated in the report. The user may then move to select another item or storage location in the report. The particular doors of the system may or may not be relocked when subsequently closed during this operation depending on the configuration of the system.

Figure 22:
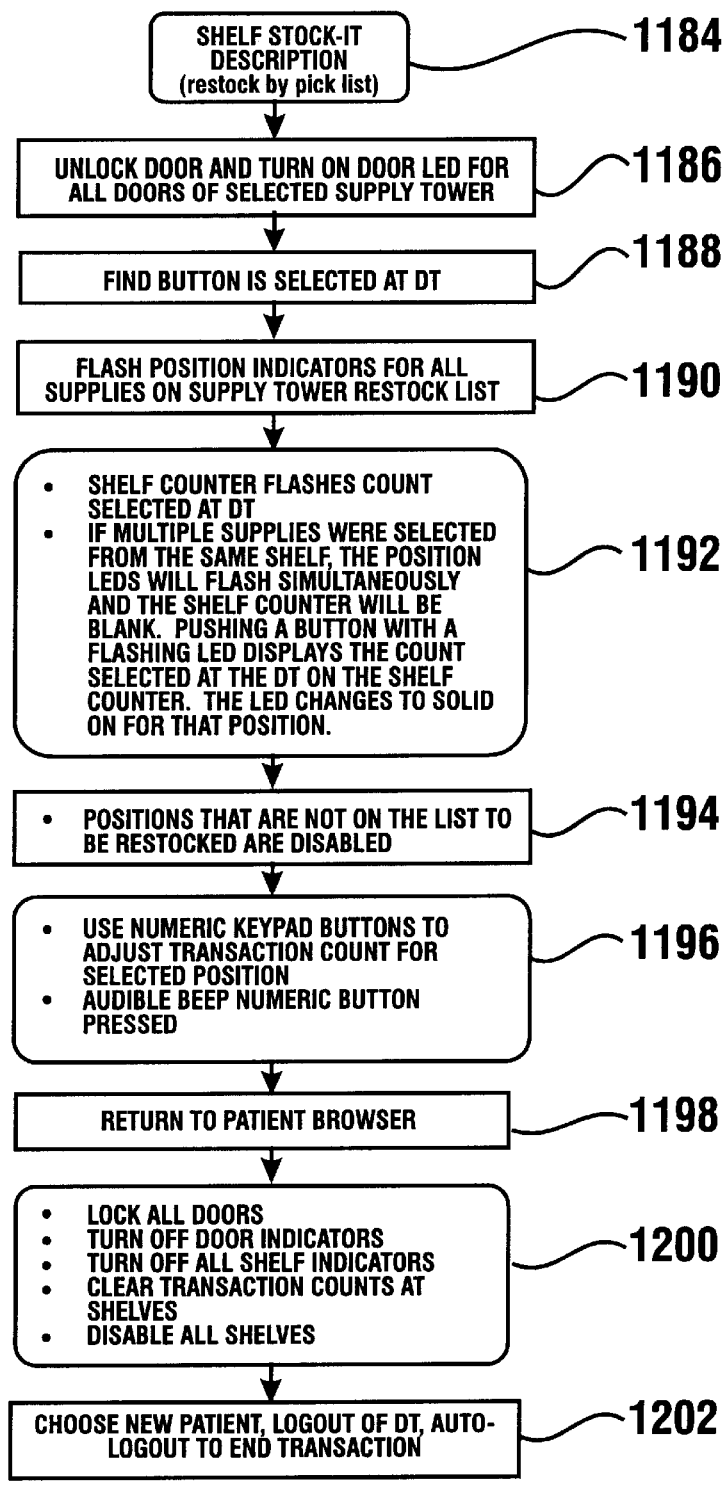

An alternative approach to restocking medical items based on a restocking list is represented by a series of steps 1184 shown in FIG. 22. In this alternative embodiment, selection of the stock it button 1172 from the patient browser screen 1020 causes all of the doors of associated cabinets where restocking is required to be unlocked and the associated door indicators to be illuminated as indicated in a step 1186 in FIG. 22. This results in the stock it screen 1178 or similar screen being displayed at the display terminal. In this alternative configuration, the item is selected for restocking by touching a particular item listed in the screen 1178 shown in FIG. 31 and by touching the accept button 1182 in a step 1188. This causes the display terminal to flash the position indicators for all of the buttons which correlate with storage locations for which restocking is indicated on the list. This is indicated as a step 1190.

As indicated as a step 1192, in situations where a single storage location is being restocked on a shelf, the shelf interface display 948 displays the count or quantity of items to be restocked. In the case where multiple locations are to be restocked on one shelf, the position indicators 942 are illuminated. Pushing the button 940 associated with each illuminated position indicator causes the shelf interface display 948 to indicate the quantity of items to be added to that particular location. As indicated in FIG. 22, the display terminal operates in a step 1194 so that during restocking, the buttons associated with storage locations that are not to be restocked are disabled.

For each storage location where restocking activity is being conducted, the user is enabled to adjust the precalculated count of the number of items to be added to a storage location. This may be accomplished through an optional step 1196 in which alternative numerical inputs indicating the quantity of items to be added to a storage location are indicated through inputs to the keypad 944 after a button corresponding to a storage location has been pressed.

Upon completion of the restock activity, the user indicates completion or that he wishes to close by pressing the "logout" button on the screen of the display terminal. This returns the screen of the display terminal to the login menu as indicated as a step 1198 and updates the information in the database. The display terminal also operates as indicated in a step 1200 to lock the doors and return the indicators to an off position while clearing all quantity indications. Also, if there are any discrepancies, a discrepancy button 1180 is provided which when activated generates a discrepancy screen enabling the user to indicate any discrepancies to the system and have the information stored in a data store. This is the same discrepancy documented earlier in the restock function using screen 1208, having the format shown in FIG. 29. As indicated by a step 1202, once the system has returned to the patient browser screen the user is enabled to select a new patient, to log out of the transaction or, alternatively, to allow the transaction to be closed through a timeout which was programmed into the operation of the display terminal.

It should be understood that the transactions mentioned in connection with the supply cabinets and system are exemplary. As can be appreciated from the foregoing discussion, numerous alternatives are available based on the teachings of the present, invention that provide advantages in the controlling and tracking of medical items.

Thus the new system and method for controlling and tracking medical items of the exemplary form of the present invention, achieves at least one of the above stated objectives, eliminates difficulties encountered in the use of prior systems and methods, solves problems and attains the desirable results described herein.

Thus the system and method of exemplary forms of the present invention achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations given herein are by way of examples and the invention is not limited to the exact details shown and described.

In addition, any feature described in the following claims as a means for performing a function shall be construed as encompassing any means known to those persons having skill in the art as being capable of performing the recited function, and shall not be deemed limited to the particular means disclosed in the foregoing description, or a mere equivalent thereof.

Having described the features, discoveries and principles of the invention, the manner in which it is constructed, operated and utilized, and the advantages and useful results attained; the new and useful structures, devices, elements, arrangements, parts, combinations, systems, equipment, operations, methods and relationships are set forth in the appended claims.

We claim:

1. A method comprising:
    (a) labeling at least one first push button among a plurality of push buttons located adjacent a front portion of a first shelf supported in a cabinet, with first button indicia, wherein the first button indicia corresponds to a first item storage location in supporting connection with the first shelf, wherein the front portion includes a plurality of visual indicators, wherein each of the plurality of buttons has a corresponding visual indicator, and wherein the first shelf comprises a first shelf display;
    (b) storing at least one of a first type medical item in the first item storage location;
    (c) providing a first manual input corresponding to the first type medical item through a terminal accessible externally relative to the cabinet, wherein at least two input devices are operative and available to receive a manual input, and wherein the at least two input devices include the at least one first push button and the terminal;
    (d) removing at least one of the first type medical item from the first item storage location;
    (e) prior to step (d), activating a first visual indicator corresponding to the at least one first push button;
    (f) prior to step (d), providing manually at least one first numerical input through the terminal corresponding to a first quantity of the first type medical item;
    (g) prior to step (d), providing a first visual output through the first shelf display corresponding to the first quantity.

2. The method according to claim 1 wherein in step (g) the first visual output is a numerical output.

3. The method according to claim 1 wherein the first shelf further comprises a take indicator, and prior to step (d) further comprising during at least a portion of performance of step (g), activating the take indicator.

4. The method according to claim 1 and further comprising:
    labeling at least one second push button among the plurality of push buttons with second button indicia, wherein the second button indicia corresponds to a second item storage location in supporting connection with the first storage shelf;
    storing at least one of a second type medical item in the second item storage location;
    providing manually at least one second numerical input through the terminal corresponding to a second quantity of the second type medical item;
    touching the at least one first push button wherein step (g) is performed responsive to such touching.

5. The method according to claim 4 further comprising:
    activating a second visual indicator corresponding to the at least one second push button responsive to at least one manual input to the terminal;
    touching the at least one push button;
    providing a second visual output through the first shelf display corresponding to the second quantity.

6. The method according to claim 5 and further comprising:
    removing the second quantity of the second type medical item from the second storage location.

7. The method according to claim 5 wherein activating the first and second indicators comprises illuminating the respective indicators.

8. The method according to claim 6 further comprising:
    (h) labeling the first item storage location with first location identifying indicia corresponding to the first button indicia;
    (i) labeling the second item storage location with second location identifying indicia corresponding to the second button indicia.

9. The method according to claim 8 wherein step (a) comprises applying a self-adhesive label having a first distinctive visual characteristic to the at least one first push button, and wherein step (h) comprises applying a self-adhesive label having the first visual characteristic to the first item storage location; and
    wherein labeling the at least one second push button with second push button indicia comprises applying a self-adhesive label having a second distinctive visual characteristic to the at least one second push button, and wherein step (i) comprises applying a self-adhesive label having the second visual characteristic to the second item storage location.

10. The method according to claim 9 wherein the first and second distinctive visual characteristics comprise different colors.

11. The method according to claim 10 wherein the cabinet comprises a plurality of shelves, and a plurality of doors, wherein each door is operative to control access to at least one shelf, and wherein a first door controls access to the first shelf, and further comprising:
    changing the first door from a locked to an unlocked condition responsive to providing the at least one manual input to the terminal in step (c).

12. The method according to claim 11 and further comprising activating at least one door indicator corresponding to the first door, responsive to providing the at least one manual input to the terminal in step (c).

13. The method according to claim 12 wherein activating the at least one door indicator comprises illuminating an indicator on the cabinet which is visible through a light guide extending through the first door.

14. The method according to claim 1 and further comprising storing data corresponding to the taking of the first quantity of the first type medical item in a data store.

15. The method according to claim 14 wherein the first shelf further comprises a first numerical keypad adjacent the first portion thereof, and further comprising:

(h) labeling at least one second push button among the plurality of push buttons with second button indicia, wherein the second button indicia corresponds to a second item storage location in supporting connection with the first shelf;

(i) storing at least one of a second type medical item in the second item storage location;

(j) touching the at least one second push button;

(k) inputting a second quantity through at least one input to the first numerical keypad;

(l) providing a second visual output through the first shelf display corresponding to the second quantity;

(m) removing the second quantity of the second type medical item from the second storage location.

16. The method according to claim 15 and further comprising:

(n) storing data in a data store representative of the taking of the second quantity of the second type medical item.

17. The method according to claim 16 wherein the first shelf comprises a clear indicator adjacent the front portion of the first shelf, and prior to step (m) further comprising, providing at least one incorrect input through the at least one push button or the keypad, and providing a manual input through the clear indicator which is operative to clear the incorrect input.

18. The method according to claim 16 and further comprising:

activating a second visual indicator corresponding to the at least one second push button responsive to performance of step (j).

19. The method according to claim 18 and further comprising:

closing a first door in supporting connection with the cabinet overlying the first shelf;

providing at least one exit input to the terminal;

locking the first door responsive to the at least one exit input.

20. The method according to claim 19 further comprising:

unlocking the first door through operation of a mechanical lock.

21. A method comprising:

(a) labeling at least one first push button among a plurality of push buttons located adjacent a front portion of a first shelf supported in a cabinet, with first button indicia, wherein the first button indicia corresponds to a first item storage location in supporting connection with the first shelf, wherein the front portion includes a plurality of first visual indicators, wherein each of the plurality of buttons has a corresponding visual indicator, and wherein the front portion includes a first numerical keypad;

(b) storing at least one of a first type medical item in the first item storage location;

(c) providing a first manual input corresponding to the first type medical item through one of at least two input devices operative and available to receive the manual input, one of the at least two input devices including the at least one first push button, and a terminal accessible externally relative to the cabinet comprises another of the at least two input devices;

(d) removing at least one of the first type medical item from the first item storage location;

(e) unlocking at least one first door in supporting connection with the cabinet and overlying the first shelf responsive to at least one input to the terminal;

(f) opening the at least one first door, wherein the input in step (c) is provided by touching the at least one first push button on the first shelf after opening the first door;

(g) subsequent to step (c), inputting a first quantity through at least one manual input to the first keypad.

22. The method according to claim 21 and further comprising:

recording the taking of the first quantity of the first type medical item in a data store.

23. The method according to claim 21 wherein the front portion of the first shelf further comprises a first shelf display, and further comprising:

displaying the first quantity through a first visual output through the first shelf display.

24. The method according to claim 23 wherein the first portion further includes a clear indicator, and further comprising:

providing an incorrect input responsive to either touching an incorrect push button or providing an incorrect quantity through the numerical keypad;

clearing the incorrect input by touching the clear indicator.

25. A method comprising:

providing a cabinet including:

a plurality of shelves, each shelf including a first item storage location and a second item storage location, a plurality of buttons on a front portion of the shelf, a plurality of visual indicators on the front portion, each visual indicator corresponding to one of the plurality of buttons, a numerical keypad on the front portion, and a shelf display on the front portion;

a plurality of lockable doors, each door having associated therewith a visual door indicator, wherein each door controls access to at least one shelf, wherein each door is inoperative connection with a mechanical and an electronic unlocking mechanism;

providing a terminal having at least one input device that is accessible externally relative to the cabinet;

labeling a first button on a shelf with first button indicia comprising a self-adhesive label having a first visual characteristic;

labeling a first storage location supported on the shelf corresponding to the first button with a self-adhesive label having the first visual characteristic;

labeling a second button on a shelf with second button indicia comprising a self-adhesive label having a second visual characteristic different from the first visual characteristic;

labeling a second storage location supported on the shelf corresponding to the second button with a self-adhesive label having the second visual characteristic;

placing a first type medical item in the first storage location;

placing a second type medical item in the second storage location;

providing at least one first type input to the terminal, the at least one first type input not indicative of a particular type medical item;

unlocking at least one door through operation of an electronic unlocking mechanism responsive to the first type input to the terminal;

providing an indication of the at least one door being unlocked through activation of at least one corresponding door indicator;

touching the first push button;

inputting a first quantity through at least one manual input to the keypad;

displaying the first quantity on the shelf display corresponding to the first push button;

taking the first quantity of the first type medical item from the first storage location;

locking the at least one door;

recording the taking of the first quantity of the first type medical item in a data store;

providing at least one second type input to the terminal, the at least one second type input being indicative of the first type medical item and a second quantity;

unlocking the first door controlling access to a shelf including the first storage location through operation of an electronic unlocking mechanism;

providing an indication of the unlocking of the first door through activation of a corresponding door indicator;

activating the visual indicator associated with the first push button;

displaying the second quantity through the shelf display on the shelf including the first storage location;

taking the second quantity of the first type medical item from the first storage location;

locking the at least one door; and recording the taking of the second quantity of the first type medical item in a data store.

26. A method comprising:

(a) labeling at least one push button with button indicia, wherein the at least one push button is among a plurality of push buttons located adjacent a front portion of a shelf supported in a cabinet, wherein the button indicia corresponds to an item storage location in supporting connection with the shelf, wherein the front portion comprises a shelf display;

(b) storing at least one of a medical item type in the item storage location;

(c) providing a manual input corresponding to the medical item type through one of at least two input devices operative and available to receive the manual input, one of the at least two input devices including the at least one push button;

(d) removing at least one of the medical item type from the item storage location;

(e) providing manually at least one numerical input to a numeric input device corresponding to a quantity of the medical item type;

(f) providing a visual output through the shelf display corresponding to the quantity.

27. The method according to claim 26 wherein the numeric input device includes a keypad, wherein step (e) comprises providing input via the keypad.

28. The method according to claim 26 wherein step (a) comprises applying a self-adhesive label having a distinctive visual characteristic to the at least one push button.

29. A method comprising:

(a) labeling at least one push button with button indicia, wherein the at least one push button is among a plurality of push buttons located adjacent a front portion of a shelf supported in a cabinet, wherein the button indicia corresponds to an item storage location in supporting connection with the shelf, wherein the front portion includes a numerical keypad;

(b) storing at least one of a medical item type in the item storage location;

(c) providing a manual input corresponding to the medical item type through one of at least two input devices operative and available to receive the manual input, one of the at least two input devices including the at least one push button;

(d) removing at least one of the medical item type from the item storage location;

(e) inputting at least one numerical input to the keypad corresponding to a quantity of the medical item type.

30. The method according to claim 29 wherein step (a) comprises applying a self-adhesive label having a distinctive visual characteristic to the at least one push button.

* * * * *